(12) United States Patent
Barros et al.

(10) Patent No.: US 10,302,631 B2
(45) Date of Patent: May 28, 2019

(54) GENETICALLY ENCODED PROBE FOR QUANTIFICATION OF PYRUVATE CONCENTRATION AND METHODS OF USING THE SAME

(71) Applicant: CENTRO DE ESTUDIOS CLENTIFICOS DE VALDIVIA, Valdivia (CL)

(72) Inventors: Luis Felipe Barros, Valdivia (CL); Sebastian Ceballo, Valdivia (CL); Alejandro San Martin, Valdivia (CL)

(73) Assignee: CENTRO DE ESTUDIOS CIENTIFICOS DE VALDIVIA, Valdivia (CL)

( * ) Notice: Subject to any disclaimer, the term of this patent is extended or adjusted under 35 U.S.C. 154(b) by 332 days.

(21) Appl. No.: 14/912,779

(22) PCT Filed: Aug. 20, 2013

(86) PCT No.: PCT/IB2013/056766
§ 371 (c)(1),
(2) Date: Feb. 18, 2016

(87) PCT Pub. No.: WO2015/025192
PCT Pub. Date: Feb. 26, 2015

(65) Prior Publication Data
US 2016/0209402 A1    Jul. 21, 2016

(51) Int. Cl.
| | |
|---|---|
| *G01N 33/50* | (2006.01) |
| *G01N 33/542* | (2006.01) |
| *G01N 21/64* | (2006.01) |
| *G01N 33/58* | (2006.01) |
| *C12Q 1/02* | (2006.01) |
| *G01N 33/64* | (2006.01) |

(52) U.S. Cl.
CPC ........... *G01N 33/5038* (2013.01); *C12Q 1/02* (2013.01); *G01N 21/6428* (2013.01); *G01N 33/5079* (2013.01); *G01N 33/542* (2013.01); *G01N 33/582* (2013.01); *G01N 33/64* (2013.01); *G01N 2021/6432* (2013.01); *G01N 2201/06113* (2013.01); *G01N 2201/12* (2013.01)

(58) Field of Classification Search
None
See application file for complete search history.

(56) References Cited

U.S. PATENT DOCUMENTS

| 7,595,375 B2 * | 9/2009 | Miyawaki | ........ | C07K 14/43595 |
| | | | | 435/252.3 |
| 7,790,868 B2 * | 9/2010 | Campbell | ........ | C07K 14/43595 |
| | | | | 435/252.1 |

FOREIGN PATENT DOCUMENTS

WO    2013154587 A1    10/2013

OTHER PUBLICATIONS

Göhler et al., "More than just a metabolic regulator—elucidation and validation of new targets of PdhR in *Escherichia coli*", BMC Systems Biology 2011, 5:197. http://www.biomedcentral.com/1752-0509/5/197.*
San Martin et al., "A Genetically Encoded FRET Lactate Sensor and Its Use to Detect the Warburg Effect in Single Cancer Cells", PLOS ONE, Feb. 2013, vol. 8, No. 2, e57712, pp. 1-11.*
Osagawara et al., "PdhR (Pyruvate Dehydrogenase Complex Regulator) Controls the Respiratory Electron Transport System in *Escherichia coli*", Journal of Bacteriology, Aug. 2007, vol. 189, No. 5, p. 5534-5541. doi:10.1128/JB.00229-07.*
Haydon et al., "A mutation causing constitutive synthesis of the pyruvate dehydrogenase complex in *Escherichia coli* is located within the pdhR gene", FEBS Lett., 1993, vol. 336, No. 1, pp. 43-47.*
Suvorova et al., "GntR Family of Bacterial Transcription Factors and Their DNA Binding Motifs: Structure, Positioning and Co-Evolution", PLOS One, 2015, 10(7):e0132618. doi:10.1371/journal. pone.0132618.*
San Martin, et al; A genetically encoded FRET lactate sensor and its use to detect the Warburg . . . ; PLoS One; 2013; vol. 8; No. 2; pp. e57712.
Trotter, et al; Reprogramming of *Escherichia coli* K-12 metabolism during the initial phase of transition . . . ; PLoS One; 2011; vol. 6; No. 9; pp. e25501.
ACZ51347; GenBank Accession No. ACZ51347; Venus + Strep tag; Cloning and transformation vector; Nov. 2009.
HQ456318; GenBank Accession No. HQ456318; Retroviral TetshRNA expression vector; Dec. 2010.
San Martin, et al; Imaging mitochondrial flux in single cells with a FRET sensor for pyruvate; PLoS One; 2014; vol. 9; No. 1; pp. e85780.
International Search Report dated Jul. 8, 2014 for PCT/IB2013/056766.

* cited by examiner

Primary Examiner — Suzanne M Noakes
(74) Attorney, Agent, or Firm — Lucas & Mercanti, LLP

(57) ABSTRACT

The present invention relates to a new optical tool for detecting and quantifying pyruvate in samples, in tissues and in cellular and subcellular compartments, with high spatial and temporal resolution, this is a Forster Resonance Energy Transfer (FRET)-based pyruvate sensor comprising a bacterial PdhR transcription factor between any suitable donor and acceptor fluorescent proteins moieties. The invention also relates to methods of use of this novel optical tool for the quantification of the activity of pyruvate transporters, for the quantification of the rates of cellular pyruvate production and consumption, and for the direct quantification of the rate of mitochondrial pyruvate consumption in intact cells.

15 Claims, 26 Drawing Sheets
Specification includes a Sequence Listing.

MAYSKIRQPKLSDVIEQQLEFLILEGTLRPGEKLPPERELAKQFDVSRP
SLREAIQRLEAKGLLLRRQGGGTFVQSSLWQSFSDPLVELLSDHPESQ
YDLLETRHALEGIAAYYAALRSTDEDKERIRELHHAIELAQQSGDLDAE
SNAVLQYQIAVTEAAHNVVLLHLLRCMEPMLAQNVRQNFELLYSRREM
LPLVSSHRTRIFEAIMAGKPEEAREASHRHLAFIEEILLDRSREESRRER
SLRRLEQRKN (SEQ ID NO: 9)

Aminoacid sequence PdhR *Escherichia coli*

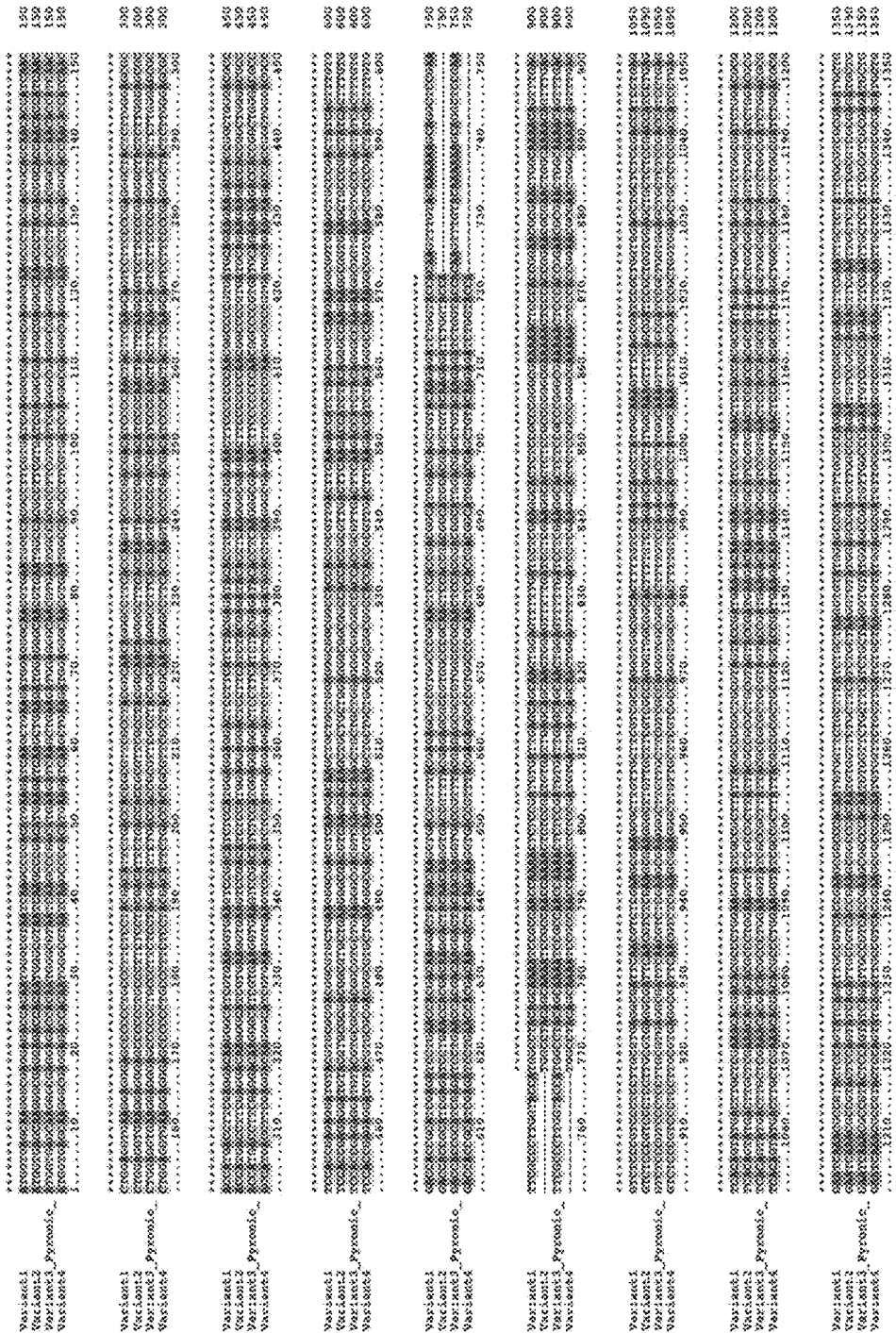
Figure 4B.1

Figure 4B.2

Bars are equivalent to 25 μm

SEQUENCE LISTING

```
<160> NUMBER OF SEQ ID NOS: 9

<210> SEQ ID NO 1
<211> LENGTH: 768
<212> TYPE: PRT
<213> ORGANISM: Escherichia coli

<400> SEQUENCE: 1

Met Val Ser Lys Gly Glu Glu Thr Thr Met Gly Val Ile Lys Pro Asp
1               5                   10                  15

Met Lys Ile Lys Leu Lys Met Glu Gly Asn Val Asn Gly His Ala Phe
            20                  25                  30

Val Ile Glu Gly Glu Gly Glu Gly Lys Pro Tyr Asp Gly Thr Asn Thr
        35                  40                  45

Ile Asn Leu Glu Val Lys Glu Gly Ala Pro Leu Pro Phe Ser Tyr Asp
    50                  55                  60

Ile Leu Thr Thr Ala Phe Ala Tyr Gly Asn Arg Ala Phe Thr Lys Tyr
65                  70                  75                  80

Pro Asp Asp Ile Pro Asn Tyr Phe Lys Gln Ser Phe Pro Glu Gly Tyr
                85                  90                  95

Ser Trp Glu Arg Thr Met Thr Phe Glu Asp Lys Gly Ile Val Lys Val
            100                 105                 110

Lys Ser Asp Ile Ser Met Glu Glu Asp Ser Phe Ile Tyr Glu Ile His
            115                 120                 125

Leu Lys Gly Glu Asn Phe Pro Pro Asn Gly Pro Val Met Gln Lys Lys
    130                 135                 140

Thr Thr Gly Trp Asp Ala Ser Thr Glu Arg Met Tyr Val Arg Asp Gly
145                 150                 155                 160

Val Leu Lys Gly Asp Val Lys His Lys Leu Leu Leu Glu Gly Gly Gly
                165                 170                 175

His His Arg Val Asp Phe Lys Thr Ile Tyr Arg Ala Lys Lys Ala Val
            180                 185                 190

Lys Leu Pro Asp Tyr His Phe Val Asp His Arg Ile Glu Ile Leu Asn
        195                 200                 205

His Asp Lys Asp Tyr Asn Lys Val Thr Val Tyr Glu Ser Ala Val Ala
    210                 215                 220

Arg Asn Ser Thr Asp Gly Met Asp Glu Leu Tyr Lys Arg Ser Gly Thr
225                 230                 235                 240

Thr Ser Leu Tyr Lys Lys Ala Gly Ser Glu Phe Ala Leu Gly Thr Met
                245                 250                 255
```

-continued

Ala Tyr Ser Lys Ile Arg Gln Pro Lys Leu Ser Asp Val Ile Glu Gln
        260                 265                 270

Gln Leu Glu Phe Leu Ile Leu Glu Gly Thr Leu Arg Pro Gly Glu Lys
        275                 280                 285

Leu Pro Pro Glu Arg Glu Leu Ala Lys Gln Phe Asp Val Ser Arg Pro
        290                 295                 300

Ser Leu Arg Glu Ala Ile Gln Arg Leu Glu Ala Lys Gly Leu Leu Leu
305                 310                 315                 320

Arg Arg Gln Gly Gly Thr Phe Val Gln Ser Ser Leu Trp Gln Ser
                325                 330                 335

Phe Ser Asp Pro Leu Val Glu Leu Leu Ser Asp His Pro Glu Ser Gln
            340                 345                 350

Tyr Asp Leu Leu Glu Thr Arg His Ala Leu Glu Gly Ile Ala Ala Tyr
        355                 360                 365

Tyr Ala Ala Leu Arg Ser Thr Asp Glu Asp Lys Glu Arg Ile Arg Glu
    370                 375                 380

Leu His His Ala Ile Glu Leu Ala Gln Gln Ser Gly Asp Leu Asp Ala
385                 390                 395                 400

Glu Ser Asn Ala Val Leu Gln Tyr Gln Ile Ala Val Thr Glu Ala Ala
                405                 410                 415

His Asn Val Val Leu Leu His Leu Leu Arg Cys Met Glu Pro Met Leu
            420                 425                 430

Ala Gln Asn Val Arg Gln Asn Phe Glu Leu Leu Tyr Ser Arg Arg Glu
        435                 440                 445

Met Leu Pro Leu Val Ser Ser His Arg Thr Arg Ile Phe Glu Ala Ile
450                 455                 460

Met Ala Gly Lys Pro Glu Glu Ala Arg Glu Ala Ser His Arg His Leu
465                 470                 475                 480

Ala Phe Ile Glu Glu Ile Leu Leu Asp Arg Ser Arg Glu Glu Ser Arg
                485                 490                 495

Arg Glu Arg Ser Leu Arg Arg Leu Glu Gln Arg Lys Asn Leu Lys Lys
            500                 505                 510

Gly Glu Phe Asp Pro Ala Phe Leu Tyr Lys Val Val Leu Lys Arg Ser
        515                 520                 525

Thr Met Val Ser Lys Gly Glu Glu Leu Phe Thr Gly Val Val Pro Ile
530                 535                 540

Leu Val Glu Leu Asp Gly Asp Val Asn Gly His Lys Phe Ser Val Ser
545                 550                 555                 560

Gly Glu Gly Glu Gly Asp Ala Thr Tyr Gly Lys Leu Thr Leu Lys Leu
                565                 570                 575

Ile Cys Thr Thr Gly Lys Leu Pro Val Pro Trp Pro Thr Leu Val Thr
            580                 585                 590

Thr Leu Gly Tyr Gly Leu Gln Cys Phe Ala Arg Tyr Pro Asp His Met
        595                 600                 605

Lys Gln His Asp Phe Phe Lys Ser Ala Met Pro Glu Gly Tyr Val Gln
    610                 615                 620

Glu Arg Thr Ile Phe Phe Lys Asp Asp Gly Asn Tyr Lys Thr Arg Ala
625                 630                 635                 640

Glu Val Lys Phe Glu Gly Asp Thr Leu Val Asn Arg Ile Glu Leu Lys
                645                 650                 655

Gly Ile Asp Phe Lys Glu Asp Gly Asn Ile Leu Gly His Lys Leu Glu
            660                 665                 670

Tyr Asn Tyr Asn Ser His Asn Val Tyr Ile Thr Ala Asp Lys Gln Lys

```
                    675                 680                 685
Asn Gly Ile Lys Ala Asn Phe Lys Ile Arg His Asn Ile Glu Asp Gly
    690                 695                 700

Gly Val Gln Leu Ala Asp His Tyr Gln Gln Asn Thr Pro Ile Gly Asp
705                 710                 715                 720

Gly Pro Val Leu Leu Pro Asp Asn His Tyr Leu Ser Tyr Gln Ser Ala
                725                 730                 735

Leu Ser Lys Asp Pro Asn Glu Lys Arg Asp His Met Val Leu Leu Glu
                740                 745                 750

Phe Val Thr Ala Ala Gly Ile Thr Leu Gly Met Asp Glu Leu Tyr Lys
                755                 760                 765

<210> SEQ ID NO 2
<211> LENGTH: 753
<212> TYPE: PRT
<213> ORGANISM: Escherichia coli

<400> SEQUENCE: 2

Met Val Ser Lys Gly Glu Glu Thr Thr Met Gly Val Ile Lys Pro Asp
1               5                   10                  15

Met Lys Ile Lys Leu Lys Met Glu Gly Asn Val Asn Gly His Ala Phe
                20                  25                  30

Val Ile Glu Gly Glu Gly Glu Gly Lys Pro Tyr Asp Gly Thr Asn Thr
            35                  40                  45

Ile Asn Leu Glu Val Lys Glu Gly Ala Pro Leu Pro Phe Ser Tyr Asp
        50                  55                  60

Ile Leu Thr Thr Ala Phe Ala Tyr Gly Asn Arg Ala Phe Thr Lys Tyr
65                  70                  75                  80

Pro Asp Asp Ile Pro Asn Tyr Phe Lys Gln Ser Phe Pro Glu Gly Tyr
                85                  90                  95

Ser Trp Glu Arg Thr Met Thr Phe Glu Asp Lys Gly Ile Val Lys Val
            100                 105                 110

Lys Ser Asp Ile Ser Met Glu Glu Asp Ser Phe Ile Tyr Glu Ile His
        115                 120                 125

Leu Lys Gly Glu Asn Phe Pro Pro Asn Gly Pro Val Met Gln Lys Lys
    130                 135                 140

Thr Thr Gly Trp Asp Ala Ser Thr Glu Arg Met Tyr Val Arg Asp Gly
145                 150                 155                 160

Val Leu Lys Gly Asp Val Lys His Lys Leu Leu Leu Glu Gly Gly Gly
                165                 170                 175

His His Arg Val Asp Phe Lys Thr Ile Tyr Arg Ala Lys Lys Ala Val
            180                 185                 190

Lys Leu Pro Asp Tyr His Phe Val Asp His Arg Ile Glu Ile Leu Asn
        195                 200                 205

His Asp Lys Asp Tyr Asn Lys Val Thr Val Tyr Glu Ser Ala Val Ala
    210                 215                 220

Arg Asn Ser Thr Asp Gly Met Asp Glu Leu Tyr Lys Arg Ser Gly Thr
225                 230                 235                 240

Met Ala Tyr Ser Lys Ile Arg Gln Pro Lys Leu Ser Asp Val Ile Glu
                245                 250                 255

Gln Gln Leu Glu Phe Leu Ile Leu Glu Gly Thr Leu Arg Pro Gly Glu
            260                 265                 270

Lys Leu Pro Pro Glu Arg Glu Leu Ala Lys Gln Phe Asp Val Ser Arg
        275                 280                 285
```

```
Pro Ser Leu Arg Glu Ala Ile Gln Arg Leu Glu Ala Lys Gly Leu Leu
290                 295                 300

Leu Arg Arg Gln Gly Gly Gly Thr Phe Val Gln Ser Ser Leu Trp Gln
305                 310                 315                 320

Ser Phe Ser Asp Pro Leu Val Glu Leu Leu Ser Asp His Pro Glu Ser
                325                 330                 335

Gln Tyr Asp Leu Leu Glu Thr Arg His Ala Leu Glu Gly Ile Ala Ala
            340                 345                 350

Tyr Tyr Ala Ala Leu Arg Ser Thr Asp Glu Asp Lys Glu Arg Ile Arg
        355                 360                 365

Glu Leu His His Ala Ile Glu Leu Ala Gln Gln Ser Gly Asp Leu Asp
    370                 375                 380

Ala Glu Ser Asn Ala Val Leu Gln Tyr Gln Ile Ala Val Thr Glu Ala
385                 390                 395                 400

Ala His Asn Val Val Leu Leu His Leu Leu Arg Cys Met Glu Pro Met
                405                 410                 415

Leu Ala Gln Asn Val Arg Gln Asn Phe Glu Leu Leu Tyr Ser Arg Arg
                420                 425                 430

Glu Met Leu Pro Leu Val Ser Ser His Arg Thr Arg Ile Phe Glu Ala
            435                 440                 445

Ile Met Ala Gly Lys Pro Glu Glu Ala Arg Glu Ala Ser His Arg His
450                 455                 460

Leu Ala Phe Ile Glu Glu Ile Leu Leu Asp Arg Ser Arg Glu Glu Ser
465                 470                 475                 480

Arg Arg Glu Arg Ser Leu Arg Arg Leu Glu Gln Arg Lys Asn Leu Lys
                485                 490                 495

Lys Gly Glu Phe Asp Pro Ala Phe Leu Tyr Lys Val Val Leu Lys Arg
            500                 505                 510

Ser Thr Met Val Ser Lys Gly Glu Glu Leu Phe Thr Gly Val Val Pro
        515                 520                 525

Ile Leu Val Glu Leu Asp Gly Asp Val Asn Gly His Lys Phe Ser Val
    530                 535                 540

Ser Gly Glu Gly Glu Gly Asp Ala Thr Tyr Gly Lys Leu Thr Leu Lys
545                 550                 555                 560

Leu Ile Cys Thr Thr Gly Lys Leu Pro Val Pro Trp Pro Thr Leu Val
                565                 570                 575

Thr Thr Leu Gly Tyr Gly Leu Gln Cys Phe Ala Arg Tyr Pro Asp His
                580                 585                 590

Met Lys Gln His Asp Phe Phe Lys Ser Ala Met Pro Glu Gly Tyr Val
            595                 600                 605

Gln Glu Arg Thr Ile Phe Phe Lys Asp Asp Gly Asn Tyr Lys Thr Arg
        610                 615                 620

Ala Glu Val Lys Phe Glu Gly Asp Thr Leu Val Asn Arg Ile Glu Leu
625                 630                 635                 640

Lys Gly Ile Asp Phe Lys Glu Asp Gly Asn Ile Leu Gly His Lys Leu
                645                 650                 655

Glu Tyr Asn Tyr Asn Ser His Asn Val Tyr Ile Thr Ala Asp Lys Gln
            660                 665                 670

Lys Asn Gly Ile Lys Ala Asn Phe Lys Ile Arg His Asn Ile Glu Asp
        675                 680                 685

Gly Gly Val Gln Leu Ala Asp His Tyr Gln Gln Asn Thr Pro Ile Gly
    690                 695                 700

Asp Gly Pro Val Leu Leu Pro Asp Asn His Tyr Leu Ser Tyr Gln Ser
```

```
                705                 710                 715                 720
Ala Leu Ser Lys Asp Pro Asn Glu Lys Arg Asp His Met Val Leu Leu
                    725                 730                 735

Glu Phe Val Thr Ala Ala Gly Ile Thr Leu Gly Met Asp Glu Leu Tyr
                    740                 745                 750

Lys

<210> SEQ ID NO 3
<211> LENGTH: 753
<212> TYPE: PRT
<213> ORGANISM: Escherichia coli

<400> SEQUENCE: 3

Met Val Ser Lys Gly Glu Glu Thr Thr Met Gly Val Ile Lys Pro Asp
1               5                   10                  15

Met Lys Ile Lys Leu Lys Met Glu Gly Asn Val Asn Gly His Ala Phe
                20                  25                  30

Val Ile Glu Gly Glu Gly Glu Gly Lys Pro Tyr Asp Gly Thr Asn Thr
            35                  40                  45

Ile Asn Leu Glu Val Lys Glu Gly Ala Pro Leu Pro Phe Ser Tyr Asp
50                  55                  60

Ile Leu Thr Thr Ala Phe Ala Tyr Gly Asn Arg Ala Phe Thr Lys Tyr
65                  70                  75                  80

Pro Asp Asp Ile Pro Asn Tyr Phe Lys Gln Ser Phe Pro Glu Gly Tyr
                85                  90                  95

Ser Trp Glu Arg Thr Met Thr Phe Glu Asp Lys Gly Ile Val Lys Val
            100                 105                 110

Lys Ser Asp Ile Ser Met Glu Glu Asp Ser Phe Ile Tyr Glu Ile His
        115                 120                 125

Leu Lys Gly Glu Asn Phe Pro Pro Asn Gly Pro Val Met Gln Lys Lys
    130                 135                 140

Thr Thr Gly Trp Asp Ala Ser Thr Glu Arg Met Tyr Val Arg Asp Gly
145                 150                 155                 160

Val Leu Lys Gly Asp Val Lys His Lys Leu Leu Leu Glu Gly Gly Gly
                165                 170                 175

His His Arg Val Asp Phe Lys Thr Ile Tyr Arg Ala Lys Lys Ala Val
            180                 185                 190

Lys Leu Pro Asp Tyr His Phe Val Asp His Arg Ile Glu Ile Leu Asn
        195                 200                 205

His Asp Lys Asp Tyr Asn Lys Val Thr Val Tyr Glu Ser Ala Val Ala
    210                 215                 220

Arg Asn Ser Thr Asp Gly Met Asp Glu Leu Tyr Lys Arg Ser Gly Thr
225                 230                 235                 240

Thr Ser Leu Tyr Lys Lys Ala Gly Ser Glu Phe Ala Leu Gly Thr Met
                245                 250                 255

Ala Tyr Ser Lys Ile Arg Gln Pro Lys Leu Ser Asp Val Ile Glu Gln
            260                 265                 270

Gln Leu Glu Phe Leu Ile Leu Glu Gly Thr Leu Arg Pro Gly Glu Lys
        275                 280                 285

Leu Pro Pro Glu Arg Glu Leu Ala Lys Gln Phe Asp Val Ser Arg Pro
    290                 295                 300

Ser Leu Arg Glu Ala Ile Gln Arg Leu Glu Ala Lys Gly Leu Leu Leu
305                 310                 315                 320

Arg Arg Gln Gly Gly Gly Thr Phe Val Gln Ser Ser Leu Trp Gln Ser
```

```
                        325                 330                 335
        Phe Ser Asp Pro Leu Val Glu Leu Leu Ser Asp His Pro Glu Ser Gln
                    340                 345                 350
        Tyr Asp Leu Leu Glu Thr Arg His Ala Leu Glu Gly Ile Ala Ala Tyr
                    355                 360                 365
        Tyr Ala Ala Leu Arg Ser Thr Asp Glu Asp Lys Glu Arg Ile Arg Glu
                370                 375                 380
        Leu His His Ala Ile Glu Leu Ala Gln Gln Ser Gly Asp Leu Asp Ala
        385                 390                 395                 400
        Glu Ser Asn Ala Val Leu Gln Tyr Gln Ile Ala Val Thr Glu Ala Ala
                        405                 410                 415
        His Asn Val Val Leu Leu His Leu Leu Arg Cys Met Glu Pro Met Leu
                    420                 425                 430
        Ala Gln Asn Val Arg Gln Asn Phe Glu Leu Leu Tyr Ser Arg Arg Glu
                    435                 440                 445
        Met Leu Pro Leu Val Ser Ser His Arg Thr Arg Ile Phe Glu Ala Ile
                450                 455                 460
        Met Ala Gly Lys Pro Glu Glu Ala Arg Glu Ala Ser His Arg His Leu
        465                 470                 475                 480
        Ala Phe Ile Glu Glu Ile Leu Leu Asp Arg Ser Arg Glu Glu Ser Arg
                        485                 490                 495
        Arg Glu Arg Ser Leu Arg Arg Leu Glu Gln Arg Lys Asn Leu Lys Arg
                    500                 505                 510
        Ser Thr Met Val Ser Lys Gly Glu Glu Leu Phe Thr Gly Val Val Pro
                    515                 520                 525
        Ile Leu Val Glu Leu Asp Gly Asp Val Asn Gly His Lys Phe Ser Val
                530                 535                 540
        Ser Gly Glu Gly Glu Gly Asp Ala Thr Tyr Gly Lys Leu Thr Leu Lys
        545                 550                 555                 560
        Leu Ile Cys Thr Thr Gly Lys Leu Pro Val Pro Trp Pro Thr Leu Val
                        565                 570                 575
        Thr Thr Leu Gly Tyr Gly Leu Gln Cys Phe Ala Arg Tyr Pro Asp His
                    580                 585                 590
        Met Lys Gln His Asp Phe Phe Lys Ser Ala Met Pro Glu Gly Tyr Val
                    595                 600                 605
        Gln Glu Arg Thr Ile Phe Phe Lys Asp Asp Gly Asn Tyr Lys Thr Arg
                610                 615                 620
        Ala Glu Val Lys Phe Glu Gly Asp Thr Leu Val Asn Arg Ile Glu Leu
        625                 630                 635                 640
        Lys Gly Ile Asp Phe Lys Glu Asp Gly Asn Ile Leu Gly His Lys Leu
                        645                 650                 655
        Glu Tyr Asn Tyr Asn Ser His Asn Val Tyr Ile Thr Ala Asp Lys Gln
                    660                 665                 670
        Lys Asn Gly Ile Lys Ala Asn Phe Lys Ile Arg His Asn Ile Glu Asp
                    675                 680                 685
        Gly Gly Val Gln Leu Ala Asp His Tyr Gln Gln Asn Thr Pro Ile Gly
                690                 695                 700
        Asp Gly Pro Val Leu Leu Pro Asp Asn His Tyr Leu Ser Tyr Gln Ser
        705                 710                 715                 720
        Ala Leu Ser Lys Asp Pro Asn Glu Lys Arg Asp His Met Val Leu Leu
                        725                 730                 735
        Glu Phe Val Thr Ala Ala Gly Ile Thr Leu Gly Met Asp Glu Leu Tyr
                    740                 745                 750
```

Lys

<210> SEQ ID NO 4
<211> LENGTH: 738
<212> TYPE: PRT
<213> ORGANISM: Escherichia coli

<400> SEQUENCE: 4

```
Met Val Ser Lys Gly Glu Glu Thr Thr Met Gly Val Ile Lys Pro Asp
1               5                   10                  15

Met Lys Ile Lys Leu Lys Met Glu Gly Asn Val Asn Gly His Ala Phe
            20                  25                  30

Val Ile Glu Gly Glu Gly Glu Gly Lys Pro Tyr Asp Gly Thr Asn Thr
        35                  40                  45

Ile Asn Leu Glu Val Lys Glu Gly Ala Pro Leu Pro Phe Ser Tyr Asp
    50                  55                  60

Ile Leu Thr Thr Ala Phe Ala Tyr Gly Asn Arg Ala Phe Thr Lys Tyr
65                  70                  75                  80

Pro Asp Asp Ile Pro Asn Tyr Phe Lys Gln Ser Phe Pro Glu Gly Tyr
                85                  90                  95

Ser Trp Glu Arg Thr Met Thr Phe Glu Asp Lys Gly Ile Val Lys Val
            100                 105                 110

Lys Ser Asp Ile Ser Met Glu Glu Asp Ser Phe Ile Tyr Glu Ile His
        115                 120                 125

Leu Lys Gly Glu Asn Phe Pro Pro Asn Gly Pro Val Met Gln Lys Lys
    130                 135                 140

Thr Thr Gly Trp Asp Ala Ser Thr Glu Arg Met Tyr Val Arg Asp Gly
145                 150                 155                 160

Val Leu Lys Gly Asp Val Lys His Lys Leu Leu Leu Glu Gly Gly Gly
                165                 170                 175

His His Arg Val Asp Phe Lys Thr Ile Tyr Arg Ala Lys Lys Ala Val
            180                 185                 190

Lys Leu Pro Asp Tyr His Phe Val Asp His Arg Ile Glu Ile Leu Asn
        195                 200                 205

His Asp Lys Asp Tyr Asn Lys Val Thr Val Tyr Glu Ser Ala Val Ala
    210                 215                 220

Arg Asn Ser Thr Asp Gly Met Asp Glu Leu Tyr Lys Arg Ser Gly Thr
225                 230                 235                 240

Met Ala Tyr Ser Lys Ile Arg Gln Pro Lys Leu Ser Asp Val Ile Glu
                245                 250                 255

Gln Gln Leu Glu Phe Leu Ile Leu Glu Gly Thr Leu Arg Pro Gly Glu
            260                 265                 270

Lys Leu Pro Pro Glu Arg Glu Leu Ala Lys Gln Phe Asp Val Ser Arg
        275                 280                 285

Pro Ser Leu Arg Glu Ala Ile Gln Arg Leu Glu Ala Lys Gly Leu Leu
    290                 295                 300

Leu Arg Arg Gln Gly Gly Gly Thr Phe Val Gln Ser Ser Leu Trp Gln
305                 310                 315                 320

Ser Phe Ser Asp Pro Leu Val Glu Leu Ser Asp His Pro Glu Ser
                325                 330                 335

Gln Tyr Asp Leu Leu Glu Thr Arg His Ala Leu Glu Gly Ile Ala Ala
            340                 345                 350

Tyr Tyr Ala Ala Leu Arg Ser Thr Asp Glu Asp Lys Glu Arg Ile Arg
        355                 360                 365
```

Glu Leu His His Ala Ile Glu Leu Ala Gln Gln Ser Gly Asp Leu Asp
            370                 375                 380

Ala Glu Ser Asn Ala Val Leu Gln Tyr Gln Ile Ala Val Thr Glu Ala
385                 390                 395                 400

Ala His Asn Val Val Leu Leu His Leu Leu Arg Cys Met Glu Pro Met
                405                 410                 415

Leu Ala Gln Asn Val Arg Gln Asn Phe Glu Leu Leu Tyr Ser Arg Arg
            420                 425                 430

Glu Met Leu Pro Leu Val Ser Ser His Arg Thr Arg Ile Phe Glu Ala
            435                 440                 445

Ile Met Ala Gly Lys Pro Glu Glu Ala Arg Glu Ala Ser His Arg His
        450                 455                 460

Leu Ala Phe Ile Glu Glu Ile Leu Leu Asp Arg Ser Arg Glu Ser
465                 470                 475                 480

Arg Arg Glu Arg Ser Leu Arg Arg Leu Glu Gln Arg Lys Asn Leu Lys
                485                 490                 495

Arg Ser Thr Met Val Ser Lys Gly Glu Leu Phe Thr Gly Val Val
            500                 505                 510

Pro Ile Leu Val Glu Leu Asp Gly Asp Val Asn Gly His Lys Phe Ser
            515                 520                 525

Val Ser Gly Glu Gly Glu Gly Asp Ala Thr Tyr Gly Lys Leu Thr Leu
    530                 535                 540

Lys Leu Ile Cys Thr Thr Gly Lys Leu Pro Val Pro Trp Pro Thr Leu
545                 550                 555                 560

Val Thr Thr Leu Gly Tyr Gly Leu Gln Cys Phe Ala Arg Tyr Pro Asp
                565                 570                 575

His Met Lys Gln His Asp Phe Phe Lys Ser Ala Met Pro Glu Gly Tyr
            580                 585                 590

Val Gln Glu Arg Thr Ile Phe Phe Lys Asp Asp Gly Asn Tyr Lys Thr
            595                 600                 605

Arg Ala Glu Val Lys Phe Glu Gly Asp Thr Leu Val Asn Arg Ile Glu
        610                 615                 620

Leu Lys Gly Ile Asp Phe Lys Glu Asp Gly Asn Ile Leu Gly His Lys
625                 630                 635                 640

Leu Glu Tyr Asn Tyr Asn Ser His Asn Val Tyr Ile Thr Ala Asp Lys
                645                 650                 655

Gln Lys Asn Gly Ile Lys Ala Asn Phe Lys Ile Arg His Asn Ile Glu
            660                 665                 670

Asp Gly Gly Val Gln Leu Ala Asp His Tyr Gln Gln Asn Thr Pro Ile
            675                 680                 685

Gly Asp Gly Pro Val Leu Leu Pro Asp Asn His Tyr Leu Ser Tyr Gln
        690                 695                 700

Ser Ala Leu Ser Lys Asp Pro Asn Glu Lys Arg Asp His Met Val Leu
705                 710                 715                 720

Leu Glu Phe Val Thr Ala Ala Gly Ile Thr Leu Gly Met Asp Glu Leu
                725                 730                 735

Tyr Lys

<210> SEQ ID NO 5
<211> LENGTH: 2307
<212> TYPE: DNA
<213> ORGANISM: artificial
<220> FEATURE:
<223> OTHER INFORMATION: synthesized

<400> SEQUENCE: 5

```
atggtgagca agggcgagga gaccacaatg ggcgtaatca agcccgacat gaagatcaag      60
ctgaagatgg agggcaacgt gaatggccac gccttcgtga tcgagggcga gggcgagggc     120
aagccctacg acggcaccaa caccatcaac ctggaggtga aggagggagc ccccctgccc     180
ttctcctacg acattctgac caccgcgttc gcctacggca cagggccctt caccaagtac     240
cccgacgaca tccccaacta cttcaagcag tccttccccg agggctactc ttgggagcgc     300
accatgacct tcgaggacaa gggcatcgtg aaggtgaagt ccgacatctc catggaggag     360
gactccttca tctacgagat acacctcaag ggcgagaact cccccccaa cggccccgtg      420
atgcagaaga agaccaccgg ctgggacgcc tccaccgaga ggatgtacgt cgcgacggc      480
gtgctgaagg cgacgtcaa gcacaagctg ctgctggagg cggcggcca ccaccgcgtt      540
gacttcaaga ccatctacag ggccaagaag gcggtgaagc tgcccgacta tcactttgtg     600
gaccaccgca tcgagatcct gaaccacgac aaggactaca acaaggtgac cgtttacgag     660
agcgccgtgg cccgcaactc caccgacggc atggacgagc tgtacaagag atctggtacc     720
acaagtttgt acaaaaaagc aggctccgaa ttcgcccttg gtaccatggc ctacagcaaa     780
atccgccaac caaaactctc cgatgtgatt gagcagcaac tggagttttt gatcctcgaa     840
ggcactctcc gcccgggcga aaaactccca ccggaacgcg aactggcaaa acagtttgac     900
gtctcccgtc cctccttgcg tgaggcgatt caacgtctcg aagcgaaggg cttgttgctt     960
cgtcgccagg gtggcggcac ttttgtccag agcagcctat ggcaaagttt cagcgatccg    1020
ctggtggagc tgctctccga ccatcctgag tcacagtatg acttgctcga acacgacac     1080
gccctggaag gtatcgccgc ttattacgcc gcgctgcgta gtaccgatga agacaaggaa    1140
cgcatccgtg aactccacca cgccatagag ctggcgcagc agtctggcga tctggacgcg    1200
gaatcaaacg ccgtactcca gtatcagatt gccgtcaccg aagcggccca caatgtggtt    1260
ctgcttcatc tgctaaggtg tatggagccg atgttggccc agaatgtccg ccagaacttc    1320
gaattgctct attcgcgtcg cgagatgctg ccgctggtga gtagtcaccg cacccgcata    1380
tttgaagcga ttatggccgg taagccggaa gaagcgcgcg aagcatcgca tcgccatctg    1440
gcctttatcg aagaaatttt gctcgacaga agtcgtgaag agagccgccg tgagcgttct    1500
ctgcgtcgtc tggagcaacg aaagaatctt aagaagggcg aattcgaccc agctttcttg    1560
tacaaagtgg tgcttaagag atctaccatg gtgagcaagg gcgaggagct gttcaccggg    1620
gtggtgccca tcctggtcga gctggacggc gacgtaaacg gccacaagtt cagcgtgtcc    1680
ggcgagggcg agggcgatgc cacctacggc aagctgaccc tgaagctgat ctgcaccacc    1740
ggcaagctgc ccgtgccctg gcccaccctc gtgaccaccc tgggctacgg cctgcagtgc    1800
ttcgcccgct accccgacca catgaagcag cacgacttct tcaagtccgc catgcccgaa    1860
ggctacgtcc aggagcgcac catcttcttc aaggacgacg gcaactacaa gacccgcgcc    1920
gaggtgaagt tcgagggcga caccctggtg aaccgcatcg agctgaaggg catcgacttc    1980
aaggaggacg gcaacatcct ggggcacaag ctggagtaca actacaacag ccacaacgtc    2040
tatatcaccg ccgacaagca gaagaacggc atcaaggcca acttcaagat ccgccacaac    2100
atcgaggacg gcggcgtgca gctcgccgac cactaccagc agaacacccc catcggcgac    2160
ggccccgtgc tgctgcccga caaccactac ctgagctacc agtccgccct gagcaaagac    2220
cccaacgaga gcgcgatca catggtcctg ctggagttcg tgaccgccgc cgggatcact    2280
```
ctcggcatgg acgagctgta caagtaa                                      2307

<210> SEQ ID NO 6
<211> LENGTH: 2262
<212> TYPE: DNA
<213> ORGANISM: artificial
<220> FEATURE:
<223> OTHER INFORMATION: synthesized

<400> SEQUENCE: 6

| | | | | | |
|---|---|---|---|---|---|
| atggtgagca | agggcgagga | gaccacaatg | gcgtaatca | agcccgacat | gaagatcaag | 60 |
| ctgaagatgg | agggcaacgt | gaatggccac | gccttcgtga | tcgagggcga | gggcgagggc | 120 |
| aagccctacg | acggcaccaa | caccatcaac | ctggaggtga | aggagggagc | cccctgccc | 180 |
| ttctcctacg | acattctgac | caccgcgttc | gcctacggca | cagggccctt | caccaagtac | 240 |
| cccgacgaca | tccccaacta | cttcaagcag | tccttccccg | agggctactc | ttgggagcgc | 300 |
| accatgacct | tcgaggacaa | gggcatcgtg | aaggtgaagt | ccgacatctc | catggaggag | 360 |
| gactccttca | tctacgagat | acacctcaag | ggcgagaact | tcccccccaa | cggccccgtg | 420 |
| atgcagaaga | agaccaccgg | ctgggacgcc | tccaccgaga | ggatgtacgt | gcgcgacggc | 480 |
| gtgctgaagg | gcgacgtcaa | gcacaagctg | ctgctggagg | gcggcggcca | ccaccgcgtt | 540 |
| gacttcaaga | ccatctacag | ggccaagaag | gcggtgaagc | tgcccgacta | tcactttgtg | 600 |
| gaccaccgca | tcgagatcct | gaaccacgac | aaggactaca | caaggtgac | cgtttacgag | 660 |
| agcgccgtgg | cccgcaactc | caccgacggc | atggacgagc | tgtacaagag | atctggtacc | 720 |
| atggcctaca | gcaaaatccg | ccaaccaaaa | ctctccgatg | tgattgagca | gcaactggag | 780 |
| tttttgatcc | tcgaaggcac | tctccgcccg | ggcgaaaaac | tcccaccgga | acgcgaactg | 840 |
| gcaaaacagt | ttgacgtctc | ccgtccctcc | ttgcgtgagg | cgattcaacg | tctcgaagcg | 900 |
| aagggcttgt | tgcttcgtcg | ccagggtggc | ggcacttttg | tccagagcag | cctatggcaa | 960 |
| agtttcagcg | atccgctggt | ggagctgctc | tccgaccatc | tgagtcaca | gtatgacttg | 1020 |
| ctcgaaacac | gacacgccct | ggaaggtatc | gccgcttatt | acgccgcgct | gcgtagtacc | 1080 |
| gatgaagaca | aggaacgcat | ccgtgaactc | caccacgcca | tagagctggc | gcagcagtct | 1140 |
| ggcgatctgg | acgcggaatc | aaacgccgta | ctccagtatc | agattgccgt | caccgaagcg | 1200 |
| gcccacaatg | tggttctgct | tcatctgcta | aggtgtatgg | agccgatgtt | ggcccagaat | 1260 |
| gtccgccaga | acttcgaatt | gctctattcg | cgtcgcgaga | tgctgccgct | ggtgagtagt | 1320 |
| caccgcaccc | gcatatttga | agcgattatg | gccggtaagc | cggaagaagc | gcgcgaagca | 1380 |
| tcgcatcgcc | atctggcctt | tatcgaagaa | attttgctcg | acagaagtcg | tgaagagagc | 1440 |
| cgccgtgagc | gttctctgcg | tcgtctggag | caacgaaaga | atcttaagaa | gggcgaattc | 1500 |
| gacccagctt | tcttgtacaa | agtggtgctt | aagagatcta | ccatggtgag | caagggcgag | 1560 |
| gagctgttca | ccggggtggt | gcccatcctg | gtcgagctgg | acggcgacgt | aaacggccac | 1620 |
| aagttcagcg | tgtccggcga | gggcgagggc | gatgccacct | acggcaagct | gaccctgaag | 1680 |
| ctgatctgca | ccaccggcaa | gctgcccgtg | cctggcccca | ccctcgtgac | caccctgggc | 1740 |
| tacggcctgc | agtgcttcgc | ccgctacccc | gaccacatga | agcagcacga | cttcttcaag | 1800 |
| tccgccatgc | ccgaaggcta | cgtccaggag | cgcaccatct | tcttcaagga | cgacggcaac | 1860 |
| tacaagaccc | gcgccgaggt | gaagttcgag | ggcgacaccc | tggtgaaccg | catcgagctg | 1920 |
| aagggcatcg | acttcaagga | ggacggcaac | atcctgggc | acaagctgga | gtacaactac | 1980 |
| aacagccaca | acgtctatat | caccgccgac | aagcagaaga | acggcatcaa | ggccaacttc | 2040 |

```
aagatccgcc acaacatcga ggacggcggc gtgcagctcg ccgaccacta ccagcagaac  2100 accccccatcg gcgacggccc cgtgctgctg cccgacaacc actacctgag ctaccagtcc  2160
gccctgagca agacccccaa cgagaagcgc gatcacatgg tcctgctgga gttcgtgacc  2220
gccgccggga tcactctcgg catggacgag ctgtacaagt aa                      2262
```

```
<210> SEQ ID NO 7
<211> LENGTH: 2262
<212> TYPE: DNA
<213> ORGANISM: artificial
<220> FEATURE:
<223> OTHER INFORMATION: synthesized

<400> SEQUENCE: 7
```

```
atggtgagca agggcgagga gaccacaatg ggcgtaatca agcccgacat gaagatcaag   60
ctgaagatgg agggcaacgt gaatggccac gccttcgtga tcgagggcga gggcgagggc  120
aagccctacg acggcaccaa caccatcaac ctggaggtga aggagggagc cccctgccc   180 ttctcctacg acattctgac caccgcgttc gcctacggca cagggcctt caccaagtac  240 cccgacgaca tccccaacta cttcaagcag tccttcccccg agggctactc ttgggagcgc  300
accatgacct tcgaggacaa gggcatcgtg aaggtgaagt ccgacatctc catggaggag  360
gactccttca tctacgagat acacctcaag ggcgagaact ccccccccaa cggccccgtg  420
atgcagaaga gaccaccgg ctgggacgcc tccaccgaga ggatgtacgt gcgcgacggc  480
gtgctgaagg gcgacgtcaa gcacaagctg ctgctggagg cggcggcca ccaccgcgtt  540 gacttcaaga ccatctacag ggccaagaag gcggtgaagc tgcccgacta tcactttgtg  600
gaccaccgca tcgagatcct gaaccacgac aaggactaca caaggtgac cgtttacgag  660 agcgccgtgg cccgcaactc caccgacggc atggacgagc tgtacaagag atctggtacc  720
acaagtttgt acaaaaaagc aggctccgaa ttcgcccttg gtaccatggc ctacagcaaa  780
atccgccaac caaaactctc cgatgtgatt gagcagcaac tggagttttt gatcctcgaa  840
ggcactctcc gcccgggcga aaaactccca ccggaacgcg aactggcaaa acagtttgac  900
gtctcccgtc cctccttgcg tgaggcgatt caacgtctcg aagcgaaggg cttgttgctt  960
cgtcgccagg gtggcggcac ttttgtccag agcagcctat ggcaaagttt cagcgatccg 1020
ctggtggagc tgctctccga ccatcctgag tcacagtatg acttgctcga acacgacac  1080 gccctggaag gtatcgccgc ttattacgcc gcgctgcgta gtaccgatga agacaaggaa 1140
cgcatccgta aactccacca cgccatagag ctggcgcagc agtctggcga tctggacgcg 1200
gaatcaaacg ccgtactcca gtatcagatt gccgtcaccg aagcggccca caatgtggtt 1260
ctgcttcatc tgctaaggtg tatggagccg atgttggccc agaatgtccg ccagaacttc 1320
gaattgctct attcgcgtcg cgagatgctg ccgctggtga gtagtcaccg cacccgcata 1380
tttgaagcga ttatgccgg taagccggaa gaagcgcgcg aagcatcgca tcgccatctg 1440
gcctttatcg aagaaatttt gctcgacaga agtcgtgaag agagccgccg tgagcgttct 1500
ctgcgtcgtc tggagcaacg aaagaatctt aagagatcta ccatggtgag caagggcgag 1560
gagctgttca ccggggtggt gcccatcctg gtcgagctgg acggcgacgt aaacggccac 1620
aagttcagcg tgtccggcga gggcgagggc gatgccacct acggcaagct gaccctgaag 1680
ctgatctgca ccaccggcaa gctgcccgtg cctggcccca cctcgtgac cacccctggg 1740 tacggcctgc agtgcttcgc ccgctacccc gaccacatga agcagcacga cttcttcaag 1800
```

| | |
|---|---|
| tccgccatgc ccgaaggcta cgtccaggag cgcaccatct tcttcaagga cgacggcaac | 1860 |
| tacaagaccc gcgccgaggt gaagttcgag ggcgacaccc tggtgaaccg catcgagctg | 1920 |
| aagggcatcg acttcaagga ggacggcaac atcctggggc acaagctgga gtacaactac | 1980 |
| aacagccaca acgtctatat caccgccgac aagcagaaga acggcatcaa ggccaacttc | 2040 |
| aagatccgcc acaacatcga ggacggcggc gtgcagctcg ccgaccacta ccagcagaac | 2100 |
| acccccatcg gcgacggccc cgtgctgctg cccgacaacc actacctgag ctaccagtcc | 2160 |
| gccctgagca agacccccaa cgagaagcgc gatcacatgg tcctgctgga gttcgtgacc | 2220 |
| gccgccggga tcactctcgg catggacgag ctgtacaagt aa | 2262 |

<210> SEQ ID NO 8
<211> LENGTH: 2217
<212> TYPE: DNA
<213> ORGANISM: artificial
<220> FEATURE:
<223> OTHER INFORMATION: synthesized

<400> SEQUENCE: 8

| | |
|---|---|
| atggtgagca agggcgagga gaccacaatg gcgtaatca gcccgacat gaagatcaag | 60 |
| ctgaagatgg agggcaacgt gaatggccac gccttcgtga tcgagggcga gggcgagggc | 120 |
| aagccctacg acgcaccaa caccatcaac ctggaggtga aggagggagc cccctgccc | 180 |
| ttctcctacg acattctgac caccgcgttc gcctacggca cagggccttc accaagtac | 240 |
| cccgacgaca tccccaacta cttcaagcag tccttccccg agggctactc ttgggagcgc | 300 |
| accatgacct tcgaggacaa gggcatcgtg aaggtgaagt ccgacatctc catggaggag | 360 |
| gactccttca tctacgagat acacctcaag ggcgagaact tcccccccaa cggccccgtg | 420 |
| atgcagaaga agaccaccgg ctgggacgcc tccaccgaga ggatgtacgt gcgcgacggc | 480 |
| gtgctgaagg gcgacgtcaa gcacaagctg ctgctggagg gcggcggcca ccaccgcgtt | 540 |
| gacttcaaga ccatctacag ggccaagaag gcggtgaagt gccccgacta tcactttgtg | 600 |
| gaccaccgca tcgagatcct gaaccacgac aaggactaca acaaggtgac cgtttacgag | 660 |
| agcgccgtgg cccgcaactc caccgacggc atggacgagc tgtacaagag atctggtacc | 720 |
| atggcctaca gcaaaatccg ccaaccaaaa ctctccgatg tgattgagca gcaactggag | 780 |
| ttttgatcc tcgaaggcac tctccgcccg ggcgaaaaac tcccaccgga acgcgaactg | 840 |
| gcaaaacagt ttgacgtctc ccgtccctcc ttgcgtgagg cgattcaacg tctcgaagcg | 900 |
| aagggcttgt tgcttcgtcg ccagggtggc ggcacttttg tccagagcag cctatggcaa | 960 |
| agtttcagcg atccgctggt ggagctgctc tccgaccatc ctgagtcaca gtatgacttg | 1020 |
| ctcgaaacac gacacgccct ggaaggtatc gccgcttatt acgccgcgct gcgtagtacc | 1080 |
| gatgaagaca aggaacgcat ccgtgaactc caccacgcca tagagctggc gcagcagtct | 1140 |
| ggcgatctgg acgcggaatc aaacgccgta ctccagtatc agattgccgt caccgaagcg | 1200 |
| gcccacaatg tggttctgct tcatctgcta aggtgtatgg agccgatgtt ggcccagaat | 1260 |
| gtccgccaga acttcgaatt gctctattcg cgtcgcgaga tgctgccgct ggtgagtagt | 1320 |
| caccgcaccc gcatatttga agcgattatg gccggtaagc cggaagaagc gcgcgaagca | 1380 |
| tcgcatcgcc atctggcctt tatcgaagaa atttttgctcg acagaagtcg tgaagagagc | 1440 |
| cgccgtgagc gttctctgcg tcgtctggag caacgaaaga atcttaagag atctaccatg | 1500 |
| gtgagcaagg gcgaggagct gttcaccggg gtggtgccca tcctggtcga gctgacggc | 1560 |
| gacgtaaacg gccacaagtt cagcgtgtcc ggcgagggcg agggcgatgc cacctacggc | 1620 |

```
aagctgaccc tgaagctgat ctgcaccacc ggcaagctgc ccgtgccctg gcccaccctc    1680
gtgaccaccc tgggctacgg cctgcagtgc ttcgcccgct accccgacca catgaagcag    1740
cacgacttct tcaagtccgc catgcccgaa ggctacgtcc aggagcgcac catcttcttc    1800
aaggacgacg gcaactacaa gacccgcgcc gaggtgaagt tcgagggcga cacgctggtg    1860
aaccgcatcg agctgaaggg catcgacttc aaggaggacg gcaacatcct ggggcacaag    1920
ctggagtaca actacaacag ccacaacgtc tatatcaccg ccgacaagca gaagaacggc    1980
atcaaggcca acttcaagat ccgccacaac atcgaggacg gcggcgtgca gctcgccgac    2040
cactaccagc agaacacccc catcggcgac ggccccgtgc tgctgcccga caaccactac    2100
ctgagctacc agtccgccct gagcaaagac cccaacgaga gcgcgatca catggtcctg    2160 ctggagttcg tgaccgccgc cgggatcact ctcggcatgg acgagctgta caagtaa       2217
```

<210> SEQ ID NO 9
<211> LENGTH: 254
<212> TYPE: PRT
<213> ORGANISM: Escherichia coli

<400> SEQUENCE: 9

```
Met Ala Tyr Ser Lys Ile Arg Gln Pro Lys Leu Ser Asp Val Ile Glu
1               5                   10                  15

Gln Gln Leu Glu Phe Leu Ile Leu Glu Gly Thr Leu Arg Pro Gly Glu
            20                  25                  30

Lys Leu Pro Pro Glu Arg Glu Leu Ala Lys Gln Phe Asp Val Ser Arg
        35                  40                  45

Pro Ser Leu Arg Glu Ala Ile Gln Arg Leu Glu Ala Lys Gly Leu Leu
    50                  55                  60

Leu Arg Arg Gln Gly Gly Gly Thr Phe Val Gln Ser Ser Leu Trp Gln
65                  70                  75                  80

Ser Phe Ser Asp Pro Leu Val Glu Leu Leu Ser Asp His Pro Glu Ser
                85                  90                  95

Gln Tyr Asp Leu Leu Glu Thr Arg His Ala Leu Glu Gly Ile Ala Ala
            100                 105                 110

Tyr Tyr Ala Ala Leu Arg Ser Thr Asp Glu Asp Lys Glu Arg Ile Arg
        115                 120                 125

Glu Leu His His Ala Ile Glu Leu Ala Gln Gln Ser Gly Asp Leu Asp
    130                 135                 140

Ala Glu Ser Asn Ala Val Leu Gln Tyr Gln Ile Ala Val Thr Glu Ala
145                 150                 155                 160

Ala His Asn Val Val Leu Leu His Leu Leu Arg Cys Met Glu Pro Met
                165                 170                 175

Leu Ala Gln Asn Val Arg Gln Asn Phe Glu Leu Leu Tyr Ser Arg Arg
            180                 185                 190

Glu Met Leu Pro Leu Val Ser Ser His Arg Thr Arg Ile Phe Glu Ala
        195                 200                 205

Ile Met Ala Gly Lys Pro Glu Glu Ala Arg Glu Ala Ser His Arg His
    210                 215                 220

Leu Ala Phe Ile Glu Glu Ile Leu Leu Asp Arg Ser Arg Glu Glu Ser
225                 230                 235                 240

Arg Arg Glu Arg Ser Leu Arg Arg Leu Glu Gln Arg Lys Asn
                245                 250
```

GENETICALLY ENCODED PROBE FOR QUANTIFICATION OF PYRUVATE CONCENTRATION AND METHODS OF USING THE SAME

CROSS REFERENCE TO RELATED APPLICATION

This Application is a 371 of PCT/IB2013/056766 filed on Aug. 20, 2013 application which is incorporated herein by reference.

FIELD OF THE INVENTION

The present invention relates to a new optical tool for detecting and quantifying pyruvate in samples, in tissues and in cellular and subcellular compartments, with high spatial and temporal resolution, this is a Forster Resonance Energy Transfer (FRED-based pyruvate sensor comprising a bacterial PdhR transcription factor between any suitable donor and acceptor fluorescent proteins moieties. The invention also relates to methods of use of this novel optical tool for the quantification of the activity of pyruvate transporters, for the quantification of the rates of cellular pyruvate production and consumption, and for the direct quantification of the rate of mitochondrial pyruvate consumption in intact cells.

BACKGROUND OF THE INVENTION

Pyruvate is an organic chemical compound that participates in the metabolism of all cells, including prokaryotes and eukaryotes. Pyruvate is a metabolic hub, situated at the cross roads of glycolysis and mitochondrial metabolism, and is the starting metabolite for multiple cellular biosynthetic pathways. Pyruvate is a molecule of great industrial interest as is currently manufactured as dietary complement, a weight control supplement and antioxidant, also being used like starting material widely applied in chemical, pharmaceutical, and agrochemical industries. Pyruvate has antioxidant properties and is thought to modulate mitochondrial redox capacity. Pyruvate is of high biomedical interest as its metabolism is altered in pathological conditions, including diabetes, neurodegenerative conditions, and cancer.

Pyruvate is in a constant state of dynamic flux between subcellular compartments, between the cell and the extracellular space and between cells. Because the concentration of pyruvate inside compartments in the living cell cannot be determined without destroying the cell, the dynamics of pyruvate in the living body is a largely unknown area.

Normal and diseased tissues are metabolically heterogeneous, showing qualitative and quantitative differences in the expression and distribution of metabolic enzymes between neighboring cells. This suggests that there may be differences between cells in terms of metabolic concentrations and fluxes for all metabolites, and specifically in terms of pyruvate concentrations and fluxes. However, this phenomenology is currently inaccessible, as current techniques to measure pyruvate are invasive and do not have sufficient sensitivity to resolve single cells.

Standard methods to measure pyruvate are based on enzymatic reactions that are monitored by means of photometric, amperometric or other devices. Enzyme-based electrodes have been developed that can detect pyruvate with high-temporal resolution. Another approach to measure pyruvate is high performance liquid chromatography (HPLC), where pyruvate is separated from other compounds by passing the sample through a stationary phase stored in a column. Nonetheless, there is a problem in the prior art, since the existing methods are invasive as they require the extraction of samples or consume pyruvate, and therefore, they change the concentration of pyruvate in the sample. A second problem of prior art methods is their sensitivity, for they cannot detect the minute amount of pyruvate present in a single cell or a single subcellular organelle. Moreover, none of the currently available methods is capable of detecting intra-cellular or sub-cellular pyruvate no-invasively in real-time or with single cell resolution. Standard methods to measure pyruvate using enzymes are cumbersome and relatively costly as they require the production and immobilization of the enzymes on a substrate and the addition of substrates and cofactors. In this regard, prior art (Staiano et al, 2007) clearly notes the difficulties for obtaining a sensor for metabolites, including for measuring pyruvate, and it remarks: "As consequence, the development of specific sensors for biochemically relevant analytes is even more challenging. In fact, it is difficult to imagine how one would design a fluorescent probe which specifically binds pyruvate, lactate, or creatinine. Even a suitable structure could be designed and synthesized, there is no guarantee that the final molecule will display a spectral change, adequate water solubility, and a suitable affinity constant."

The transport of pyruvate across cellular and subcellular membranes is mediated by specific membrane transporters, molecules involved in the pathogenesis of several diseases and an important target for pharmacological intervention in cancer and diabetes. There are no available methods to measure the transport of pyruvate in single cells. More specifically, current and common techniques to measure the transport of pyruvate using radioactive isotopes cannot resolve single cells and have poor temporal resolution, which hampers the study fast phenomena and of normal tissues, which are heterogeneous in their cellular composition. An existing technique is indirect and infers the transport of pyruvate in single cells from changes in pH that accompany the transport of pyruvate, but this technique is limited insofar as requires prior knowledge of the usually unknown buffering capacity of the cell and is not easily applicable in the presence of physiological bicarbonate buffers.

The rates of pyruvate production and pyruvate consumption are important parameters of cell metabolism, with relevance for hypoxia/ischemia, cancer, diabetes, mitochondrial diseases and other pathological conditions. There are no available methods to measure the rates of pyruvate production and consumption in single cells. More specifically, current and common techniques to measure the rates of pyruvate production and consumption are enzyme-based methods that cannot resolve single cells and have poor temporal resolution. Measurements using isotopes cannot resolve single cells and have poor sensitivity and temporal resolution.

Pyruvate is the main substrate for mitochondria, and the speed of pyruvate metabolism is tightly linked to the speed of cellular respiration. These are fundamental parameters of cell metabolism and are affected in several diseases including hypoxic/ischemia, cancer, diabetes and other conditions. Assessment of the speed of mitochondrial metabolism is an early step in the development of pharmaceutical drugs, which is required to rule out drug candidates that may cause adverse effects on metabolism. There are no available methods to measure the rate of pyruvate consumption by mitochondria in intact cells, in single cells or in real time. Current and common techniques for measuring the rates of mitochondrial pyruvate consumption use isotopes that cannot resolve single cells and have poor sensitivity and low temporal resolution.

An existing technique based on a genetically-encoded sensor for lactate estimates the consumption of lactate in single cells (PCT/US 12/33639 from the same Applicant, not yet published). Pyruvate and lactate are linked by the enzyme lactate dehydrogenase (LDH), which catalyzes a reaction involving NADH, NAD+ and pH. Thus, the indirect estimation of pyruvate mitochondrial consumption using lactate measurement is limited insofar as may be affected in unpredictable manner by other mechanisms affecting the activity of LDH or by the concentrations of NADH, $NAD^+$ or by intracellular pH. Another limitation of using said lactate sensor is that lactate is also a substrate for mitochondria (Brooks, 2009), so it is not possible to ascertain with the lactate sensor how much pyruvate is being consumed and how much lactate is being consumed. Moreover, the lactate sensor may not be calibrated in cells easily, which makes quantitative measurements of lactate impractical, reason why it has been recommended that its use be only qualitative or semiquantitative (San Martin et al., 2013). On the contrary, in the first place, the sensor of the present invention provides a direct measure of pyruvate concentration, while secondly, the sensor of the present invention can be easily calibrated in non-invasive form; thus providing quantitative measurement of pyruvate concentration and pyruvate fluxes. Thirdly, the estimation of flux is not affected by unpredictable variations in LDH activity and/or $NADH/NAD^+$ ratio or by intracellular pH.

DISCLOSURE OF THE INVENTION

Technical Problems to be Solved

The subject of the present invention is to provide a genetically encoded probe, which allows minimally-invasive measurement of pyruvate with high sensitivity, which does not consume pyruvate during measurement, and that can be used to measure pyruvate in samples, in cells and in subcellular compartments, with improved spatiotemporal resolution as part of the most relevant contributions in respect to the prior art. Further, the subject of the present invention is to provide a measuring method of pyruvate using the genetically encoded probe, a method to measure the activity of the pyruvate transporters, a method to measure the rates of cellular pyruvate production and pyruvate consumption, and a method to measure the rate of pyruvate consumption by mitochondria in intact cells.

BRIEF DESCRIPTION OF THE INVENTION

In the first embodiment of the present invention, inventors have generated a genetically encoded probe, also referred herein as "Pyronic", for efficiently measuring pyruvate levels. This probe has been particularly designed for pyruvate. Further, Pyronic is a fluorescence resonance energy transfer (FRET)-based sensor consisting of the bacterial PdhR transcription factor sandwiched between the fluorescent proteins mTFP and Venus. Pyronic showed shows a monophasic dose response curve with apparent dissociation constant for pyruvate of 107±13 µM, which allows accurate quantitation of pyruvate between 10 µM and 1 mM, spanning the concentration range found in normal and diseased cells. This invention also encompasses methods for the measurement of pyruvate transport activity and of two metabolic rates, the rate of pyruvate production/consumption and the rate of pyruvate consumption by mitochondria in intact cells. These methods can be applied to single cells or cell populations, cells in suspension or adherent, to a cell culture, a tissue culture, a mixed cell culture, a tissue explant, or it can also be applied to animal tissues in vivo. The above-mentioned methods include the expression of Pyronic in individual, prokaryotic or eukaryotic cells, and also its use as a free molecule in solution or attached to a substrate.

Pyronic can be expressed in single cells or cell populations, cells in suspension or adherent, in a cell culture, a tissue culture, a mixed cell culture, a tissue explant, or in animal tissues in vivo. The gene expression can be attained by any suitable method known in the art to transfer the sensor gene information to the host cell. Examples of gene transfer methodologies may be plasmid transfer using liposomal delivery, virus transfer, and transgenesis. The person skilled in the art would easily recognize any suitable transformation technologies to assure Pyronic expression. Once the sensor is expressed in single cells or cell populations, cells in suspension or adherent, in a cell culture, a tissue culture, a mixed cell culture, a tissue explant, or in animal tissues in vivo, the sensor is calibrated according to pre-established conditions.

Additionally to being expressed within the above mentioned cells or tissues, the sensor can also be released from the cells or tissues using a suitable technology and used as a free molecule in solution or attached to a substrate, where it is calibrated according to pre-established conditions. Again, the person skilled in the art would easily recognize any suitable technologies in order to release Pyronic from the cells or tissues.

On a second embodiment, this invention provides a method to measurement the activity of the pyruvate transporter. Using the information obtained in the calibration step, the determination of the activity of the pyruvate transporter is carried out by exposing the cells to pyruvate. This causes a rise in intracellular pyruvate that is monitored with the pyruvate sensor and whose initial rate is independent of pyruvate metabolism and can be used to estimate kinetic parameters. Exposure of the cells to increasing concentrations of pyruvate allows the estimation of kinetic parameters for the pyruvate transporter. Kinetic parameters are also obtained from the decrease in intracellular pyruvate after removal of extracellular pyruvate.

On a third embodiment, the present application features a method to measure the rates of pyruvate production and pyruvate consumption. With the information obtained in the calibration step, the determination of the rates of pyruvate production or consumption is carried out by disrupting the flux of pyruvate, which is normally maintained in a steady-state.

To quantitate the rate of cellular pyruvate production or consumption, the steady-state is disrupted by addition of a blocker of the pyruvate transporter. In mammalian cells, the surface pyruvate transporter is the monocarboxylate transporter (MCT) and can be blocked with phloretin, parachloromercurybenzoate, AR-C155858 or other suitable compounds. If the cell is net pyruvate producer, application of the MCT-blocker causes an acute increase in intracellular pyruvate concentration, the initial rate of which is equal to the rate of cellular pyruvate production in the steady-state. On the other hand, if the cell is a net pyruvate importer, application of the MCT-blocker causes a fall in intracellular pyruvate concentration, the initial rate of which is equal to the rate of pyruvate consumption on the steady-state. In another embodiment, the disruption of the steady-state is attained by adding an inhibitor of the MCT, such as, but not limited to phloretin, parachloromercurybenzoate, AR-C155858, anti-MCl antisera, etc. In prokaryotic cells and other cells wherein pyruvate transport is mediated by other transporters, the method can be applied using their respective inhibitors. A critical property of Pyronic that allows quantitation of these rates is its high temporal resolution, for only the initial rate of pyruvate accumulation is informative and after a few seconds other non-linear processes like inhibition of glycolysis by the increasing pyruvate or changes in mitochondrial pyruvate uptake may interfere with the measurement. Because of its low temporal resolution, extracellular pyruvate measurement by existing techniques cannot be used in combination with transporter-blockage to estimate the rates of pyruvate production or pyruvate consumption.

In a fourth embodiment, this invention also provides methods to measure the rate of mitochondrial pyruvate consumption. With the information obtained in the calibration step, the determination of the rate of pyruvate consumption by mitochondria is carried out by disrupting the flux of pyruvate, which is normally maintained in a steady-state. The method involves exposing the cells to pyruvate as exclusive metabolic substrate. Under such conditions cells take up pyruvate at a rate equal to the rate of pyruvate consumption by mitochondria, and after acute application of an inhibitor of the surface pyruvate transporter such as phloretin, parachloromercurybenzoate, AR-C155858, anti-MCT antisera, or other suitable compound, follows a decrease in intracellular pyruvate concentration at a rate equal to the rate of mitochondrial pyruvate consumption. In prokaryotic cells and other cells were pyruvate transport is mediated by other transporters, the method can be applied using their respective inhibitors. In a variant of this inhibitor-stop method, mitochondrial pyruvate flux can be estimated in a single mitochondrion. The pyruvate sensor is expressed in mitochondria, for example by using a sequence of mitochondrial destination. The steady-state is then perturbed by inhibiting the mitochondrial pyruvate carrier (MPC), for example with the specific MPC blocker UK-5099, which shall produce a decrease in intramitochondrial pyruvate concentration at a rate equal to the rate of pyruvate consumption. This protocol does not need manipulation of substrate and will give the rate of pyruvate consumption at physiological cytosolic pyruvate.

Summarizing, the methods provided by the present invention share the following steps:
  Provide a system for the measurement of pyruvate and/or rate of pyruvate production or consumption and/or the rate of mitochondrial pyruvate consumption. The system can be used in single cells or cell populations, cells in suspension or adherent, a cell culture, a tissue culture, a mixed cell culture, a tissue explant, or animal tissues in vivo. The sensor can also be used as a free molecule in solution or attached to a substrate;
  Express the pyruvate sensor Pyronic in individual cells and/or in subcellular compartments such as mitochondria, or as a free molecule or attached to a substrate;
  Calibrate the sensor in the controlled conditions;
  Measure the activity of the pyruvate transporter by exposing cells to varying concentrations of extracellular pyruvate;
  Measure metabolic rates by disrupting the steady-state of pyruvate by:
    Adding a blocker of the mitochondrial pyruvate transporter, this measures the instantaneous rate of pyruvate consumption by mitochondria, and/or
    Adding an MCT inhibitor in the exclusive presence of pyruvate, this gives a prolonged measurement of the rate of mitochondrial pyruvate consumption;
  Record the output from the sensor and calculate the corresponding pyruvate concentration at different times; and
  Determine the rates of transport and the metabolic rates.

BRIEF DESCRIPTION OF THE DRAWINGS

The invention is illustrated by the accompanying drawings wherein:

FIG. 2 shows the aminoacid sequence of PdhR from *E. coli*.

FIG. 4A shows the aminoacid sequences of four variants of the pyruvate sensor, identified as SEQ ID NO: 1, SEQ ID NO: 2, SEQ ID NO: 3 and SEQ ID NO: 4.

FIGS. 4B.1 and 4B.2 show the DNA sequences of four variants of the pyruvate sensor, identified as SEQ ID NO: 5, SEQ ID NO: 6, SEQ ID NO: 7 and SEQ ID NO: 8.

DETAILED DESCRIPTION OF THE INVENTION

Figure 1:
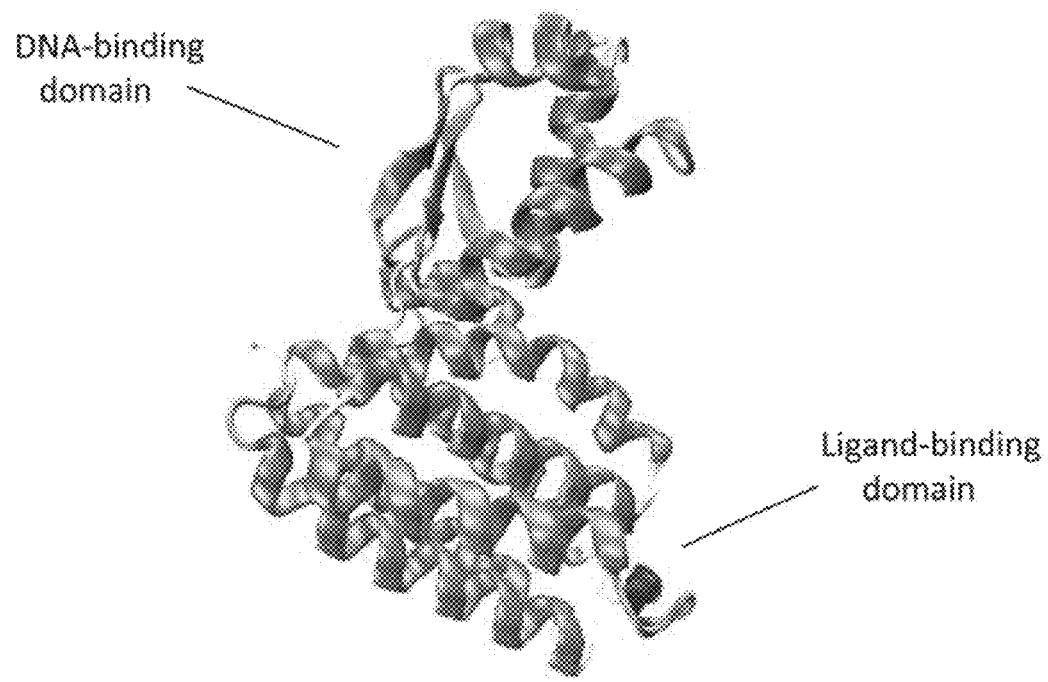
FIG. 1 shows the predicted tridimensional structure of the transcriptional regulator PdhR from *Escherichia coli* (*E. coli*).

The invention refers to a Forster Resonance Energy Transfer (FRET)-based pyruvate sensor comprising a bacterial PdhR transcription factor between any suitable donor and acceptor fluorescent proteins moieties that are capable in combination of serving as donor and acceptor moieties in FRET, which can be expressed in single cells or cell populations, adherent cells or in suspension, in a cell culture, a tissue culture, a mixed cell culture, a tissue explant, or in animal tissues in vivo. Also the invention is related to a method for the measurement of pyruvate wherein the method comprises the steps of:
a. Expressing a FRET-based pyruvate sensor of the invention in a desired host, such as single cells or cell populations, adherent cells or in suspension, in a cell culture, a tissue culture, a mixed cell culture, a tissue explant, or in animal tissues in vivo;
b. Calibrating the host with predetermined values of intracellular, extracellular, subcellular pyruvate concentrations, recording pyruvate concentrations in time;
c. Disrupting the steady-state of pyruvate in the cell;
d. Recording the output from the sensor calculating the pyruvate concentration at different time points and determining the rates of transport.

In another hand the invention is related to a method for the measurement of the rate of pyruvate production or consumption wherein the method comprises the steps of:
a. Expressing a FRET-based pyruvate sensor of the invention in a desired host, such as single cells or cell populations, adherent cells or in suspension, in a cell culture, a tissue culture, a mixed cell culture, a tissue explant, or in animal tissues in vivo;
b. Calibrating the host with predetermined values of intracellular, extracellular, subcellular pyruvate concentrations, recording pyruvate concentrations in time;
c. Disrupting the steady-state of pyruvate in the cell;
d. Recording the output from the sensor calculating the pyruvate concentration at different time points and determining the rates of transport.

Finally the invention refers to a method for the measurement of the rate of mitochondrial pyruvate consumption wherein the method comprises the steps of:
a. Expressing a FRET-based pyruvate sensor of the invention in a desired host, such as single cells or cell populations, adherent cells or in suspension, in a cell culture, a tissue culture, a mixed cell culture, a tissue explant, or in animal tissues in vivo;
b. Calibrating the host with predetermined values of intracellular, extracellular, subcellular pyruvate concentrations, recording pyruvate concentrations in time;
c. Disrupting the steady-state of pyruvate in the cell;
d. Recording the output from the sensor calculating the pyruvate concentration at different time points and determining the rates of transport.

The following detailed description refers to the accompanying drawings. While embodiments of the sensor of the invention may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the scope of the invention. While the sensor and the methods are described in terms of "comprising" various elements or steps, the sensor and the methods can also "consist essentially of" or "consist of" the various elements or steps, unless stated otherwise. Additionally, the terms "a," "an," and "the" are intended to include plural alternatives, e.g., at least one, unless stated otherwise.

The sensor quantifies pyruvate between 10 μM and 1 mM, allowing measurement of pyruvate in samples in the absence of cells and also single-cell measurement of pyruvate concentration, pyruvate transporter activity, pyruvate production, pyruvate consumption, and the rate of mitochondrial pyruvate consumption.

The sensor of the present invention is a Forster Resonance Energy Transfer (FRED-based pyruvate sensor further consisting on PdhR, a bacterial transcription regulator that has two modules, a pyruvate-binding/regulatory domain and a DNA-binding domain. The PdhR gene was isolated from *Escherichia coli* (FIG. 1 and FIG. 2).

The inventors have developed the pyruvate sensor using the PdhR gene, wherein in general terms, the sensor comprises the following structural sequence: A Donor FRET moiety, followed by, optionally, linker 1; PdhR (including both domains); optionally, linker 2; and an Acceptor FRET moiety.

The FRET-based pyruvate sensor of the invention may incorporate any suitable donor and acceptor fluorescent proteins moieties that are capable in combination of serving as donor and acceptor moieties in FRET. Preferred donor and acceptor moieties are selected from the group consisting of mTFP (monomeric teal fluorescent protein), CFP (cyan fluorescent protein), BFP (blue fluorescent protein), GFP (green fluorescent protein), YFP (yellow fluorescent protein), enhanced variations thereof such as enhanced YFP (EYFP), Citrine or Venus, or infrared fluorescent proteins from bacterial and plant phytochromes, with a particularly preferred embodiment provided by the donor/acceptor mTFPNenus. Criteria to consider when selecting donor and acceptor fluorescent moieties is known in the art, for instance as disclosed in U.S. Pat. No. 6,197,928, which is herein incorporated by reference in its entirety. In an alternative embodiment, it can be used a single fluorescent moiety such as circularly-permuted variations of GFP (Akerboom et al., 2009) inserted into the backbone of PdhR or other suitable pyruvate-binding protein, which undergoes a change in fluorescence intensity in response to binding of pyruvate to the PdhR moiety or to other suitable pyruvate-binding protein.

In a more preferred embodiment, the FRET pair selected was mTFP and Venus, which compared with CFP and YFP are respectively brighter and less pH-sensitive.

The inventors have developed four preferred embodiments of the sensor of the present invention, wherein each of them has the following configuration:
1—mTFP (donor) located at the N-terminus, followed by linker 1, PdhR, linker 2, and Venus (Acceptor) located at the C-terminus (amino acid sequence SEQ ID NO 1; nucleic acid sequence SEQ ID NO 5);

2—mTFP (donor) located at the N-terminus, followed by PdhR, linker 2, and Venus (Acceptor) located at the C-terminus (amino acid sequence SEQ ID NO 2; nucleic acid sequence SEQ ID NO 6);

3—mTFP (donor) located at the N-terminus, followed by linker 1, PdhR, and Venus (Acceptor) located at the C-terminus (amino acid sequence SEQ ID NO 3; nucleic acid sequence SEQ ID NO 7);

4—mTFP (donor) located at the N-terminus, followed by PdhR, and Venus (Acceptor) located at the C-terminus (amino acid sequence SEQ ID NO 4; nucleic acid sequence SEQ ID NO 8).

Figure 3:
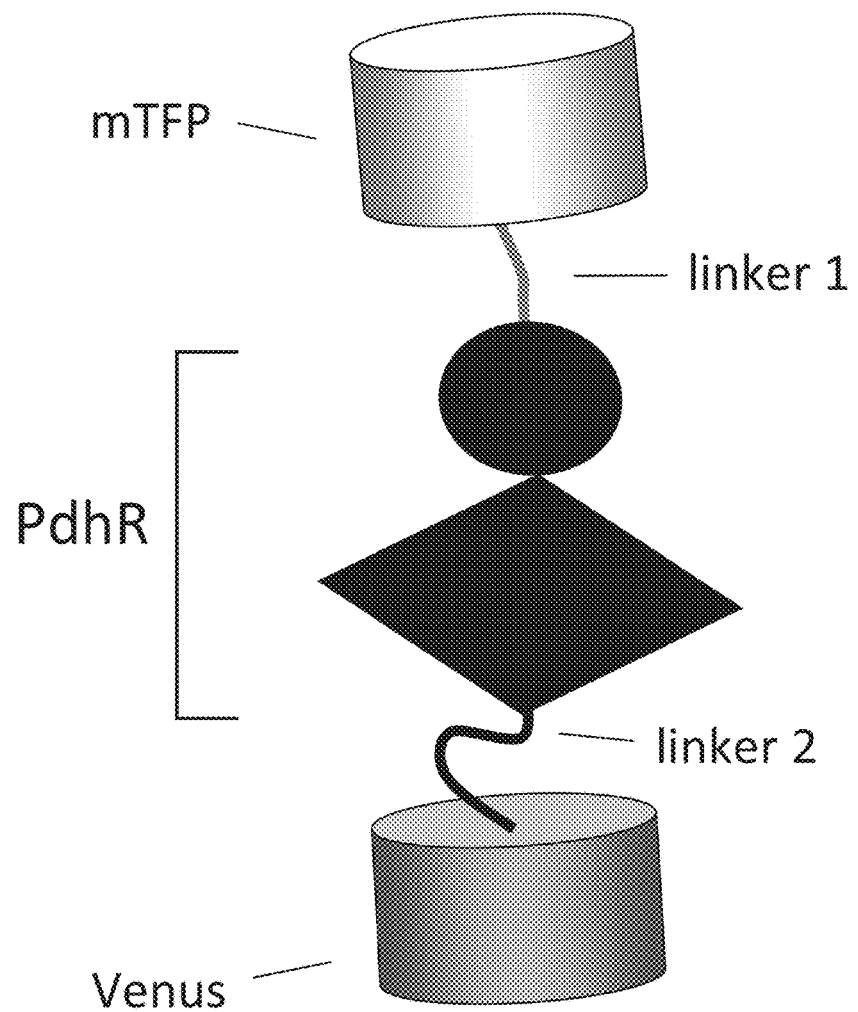
FIG. 3 schematically illustrates the general plan for the construction of the pyruvate sensor.

The architecture of the four sensors are shown in FIG. 3, with mTFP (donor) located at the N-terminus, the PdhR flanked by linkers, and Venus (Acceptor) located at the C-terminus.

Figure 4B.2:
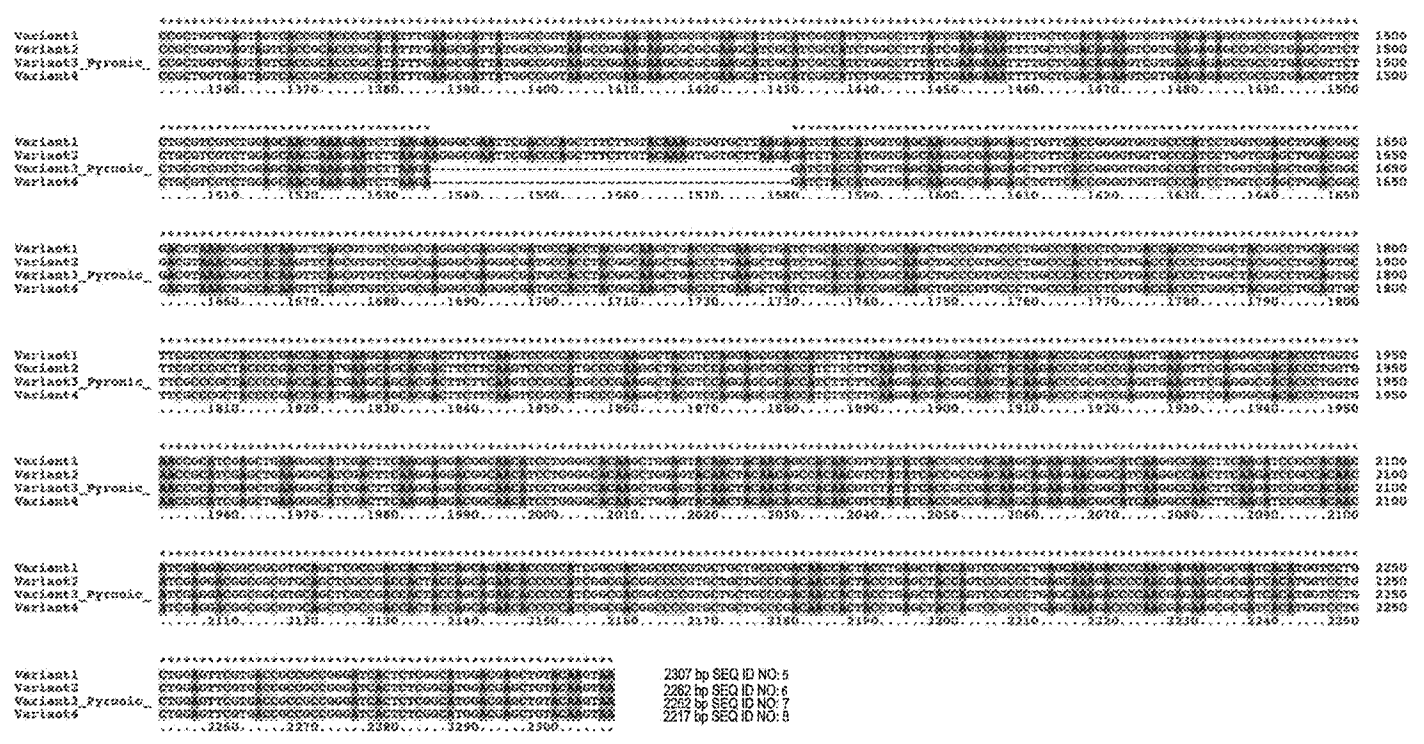

In a further embodiment, the present invention includes pyruvate sensors described according to the amino acid sequences and have at least 60%, 70%, 80%, 85%, 90%, 95%, or 99% sequence identity with SEQ ID NO 1, SEQ ID NO 2, SEQ ID NO 3 or SEQ ID NO 4 (FIG. 4). The present invention also covers pyruvate sensors encoded by the nucleic acid sequences having at least 60%, 70%, 80% 85%, 90%, 95%, or 99% sequence identity with SEQ ID NO 5, SEQ ID NO 6, SEQ ID NO 7 or SEQ ID NO 8 (FIG. 4).

Figure 5:
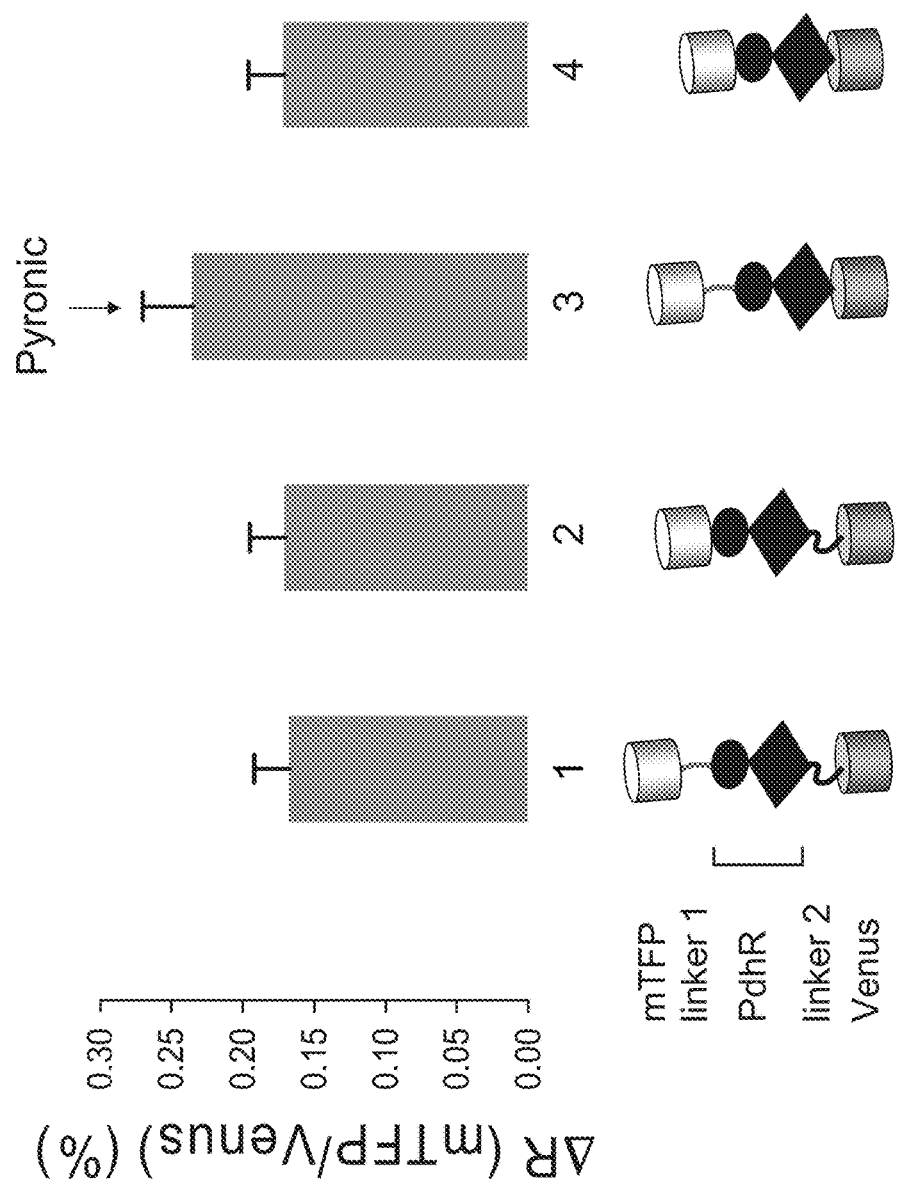
FIG. 5 shows the response to pyruvate of four variants of the pyruvate sensor, the most responsive is termed Pyronic.
Figure 6:
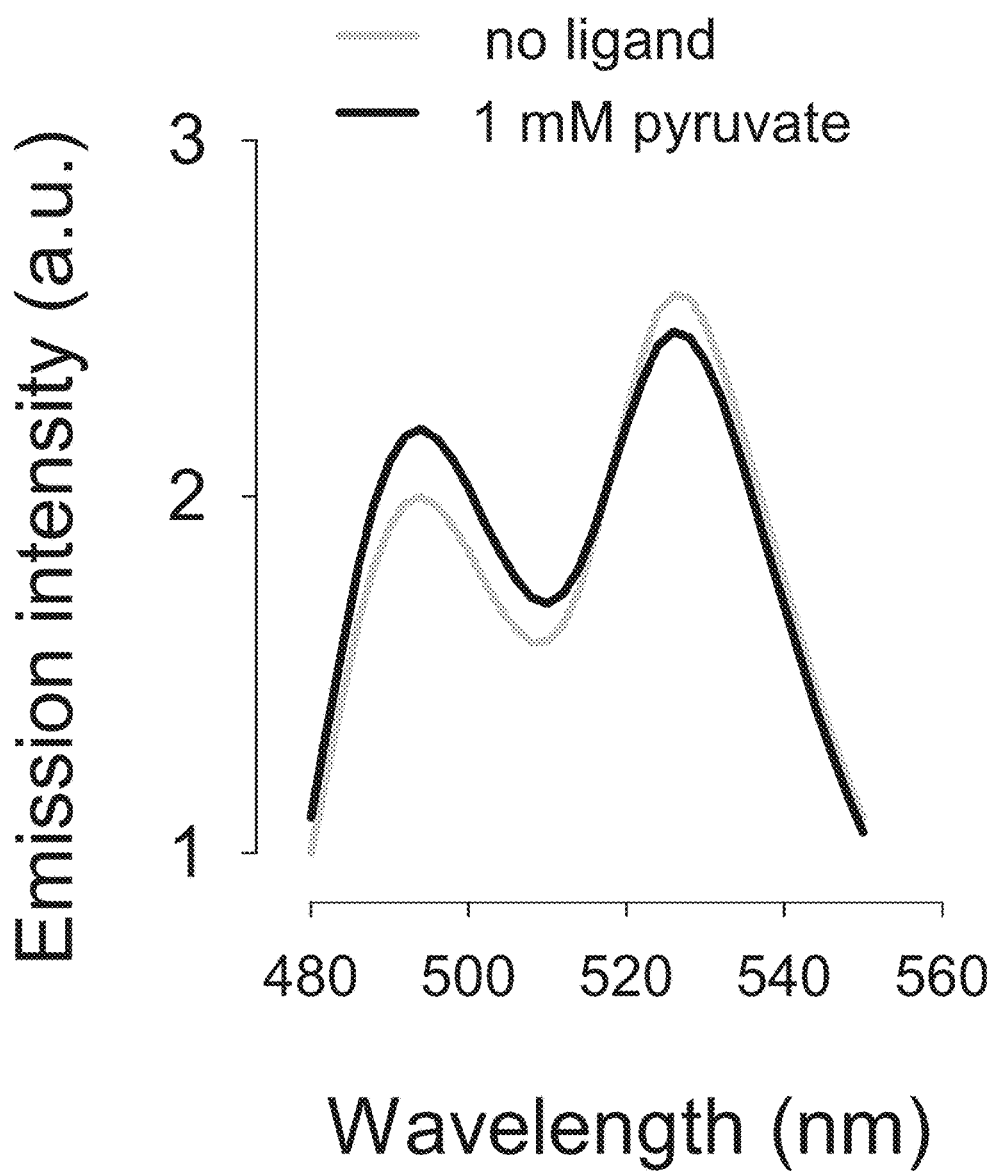
FIG. 6 shows the effect of pyruvate on the fluorescence emission spectrum of Pyronic.
Figure 7:
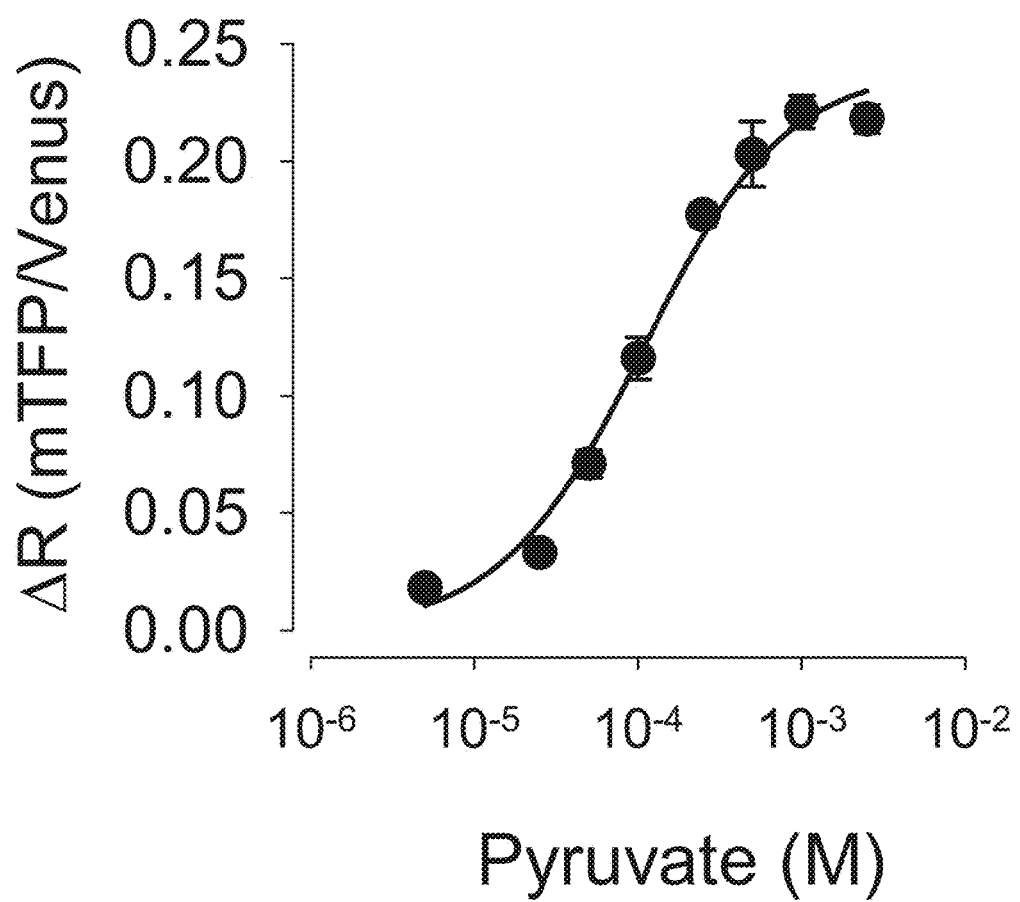
FIG. 7 presents the change in fluorescence ratio of Pyronic in response to increasing concentrations of pyruvate.

The sequences described in SEQ ID NO 1 to SEQ ID NO 4 are only particular embodiments of the present invention provided as way of exemplification of the present invention, and should not be considered to limit the scope of the invention. The proteins corresponding to sequences ID 1, ID 2, ID 3 and ID 4 were expressed in *Escherichia coli*, then purified and exposed a high concentration of pyruvate. The four proteins responded to pyruvate with a significant change in the ratio of fluorescence intensity between mTFP and Venus (FIG. 5). The most responsive variant, arrowed in FIG. 4, was termed Pyronic and was chosen for further characterization. It contains the full length PdhR from *E. coli* and one linker. The emission spectrum of this sensor showed the expected peaks of mTFP and Venus at 492 nm and 526 nm, respectively (FIG. 6). The affinity constant of PdhR for pyruvate is not known. FIG. 6 shows that Pyronic responded to increasing pyruvate concentrations with increasing values of ratio between mTFP and Venus fluorescence intensity. Fluorescence intensity (at 430 nm excitation) was measured at increasing pyruvate concentrations, and the behavior was well represented by a single rectangular hyperbola, with apparent dissociation constant (KD) value of 107±13 μM, and respective maximum ΔR value of about 20% (FIG. 7). These kinetic parameters of the sensor confer the desirable ability of reporting intracellular pyruvate between 10 μM and 1 mM, thus across physiological and pathological levels, which in mammalian cells oscillate around 20-40 μM.

Figure 8:
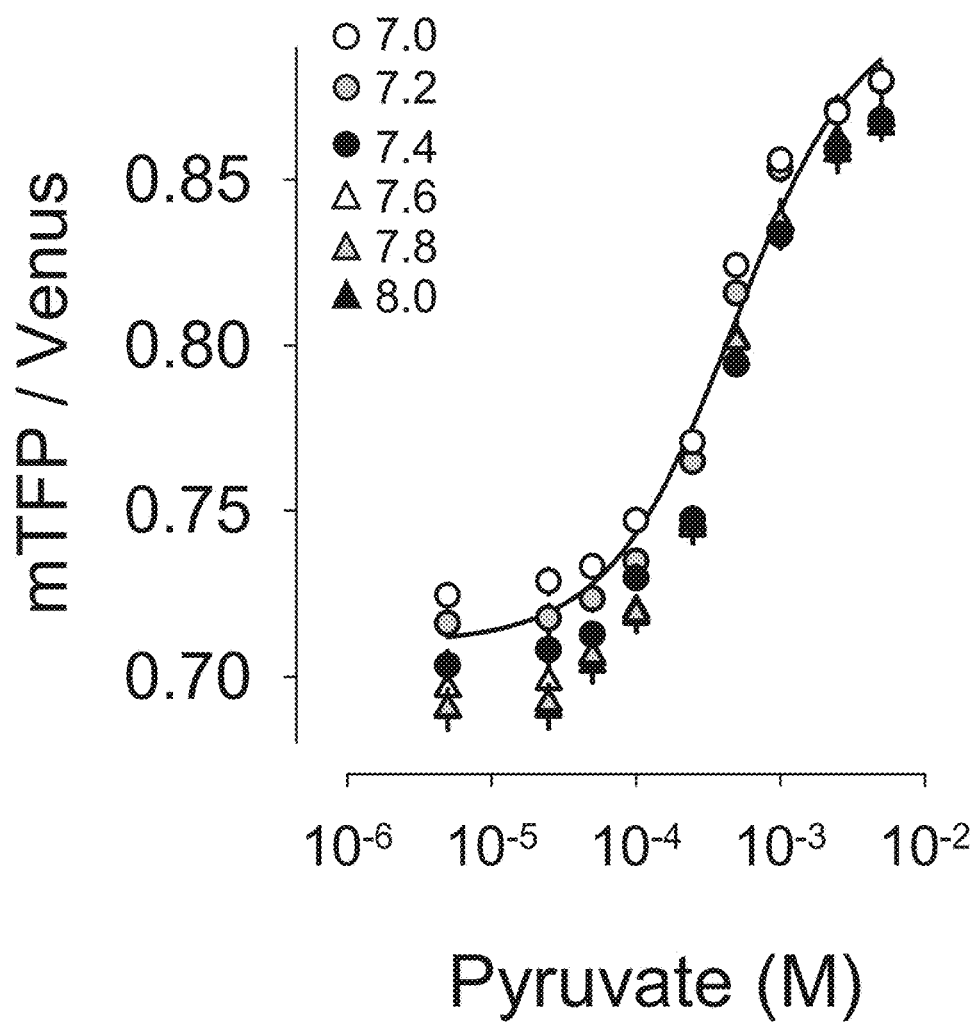
FIG. 8 shows the effect of pH on the response of Pyronic to pyruvate.
Figure 9:
FIG. 9 shows the effect of several molecules on the fluorescence ratio of Pyronic.
Figure 10:
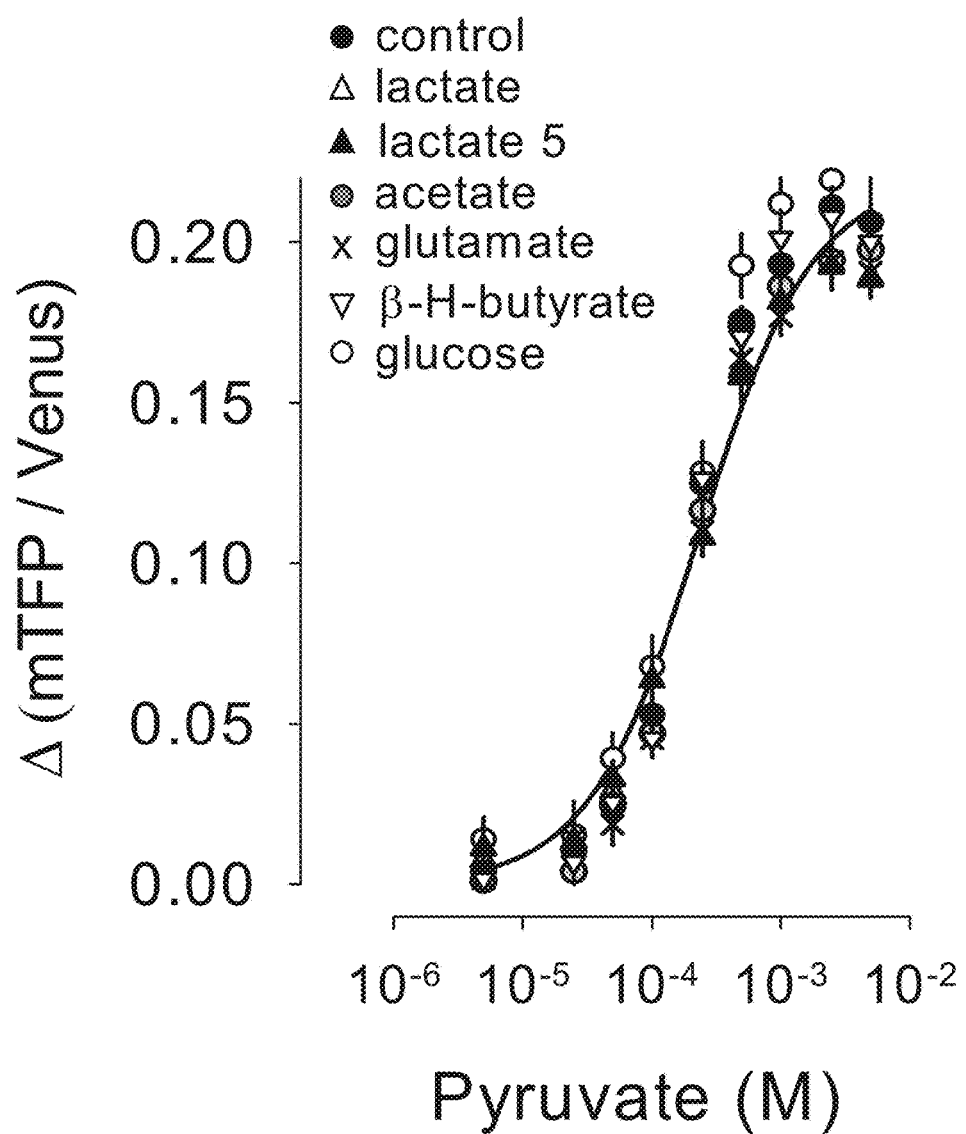
FIG. 10 shows the effect of several molecules on the response of Pyronic to pyruvate.
Figure 11:
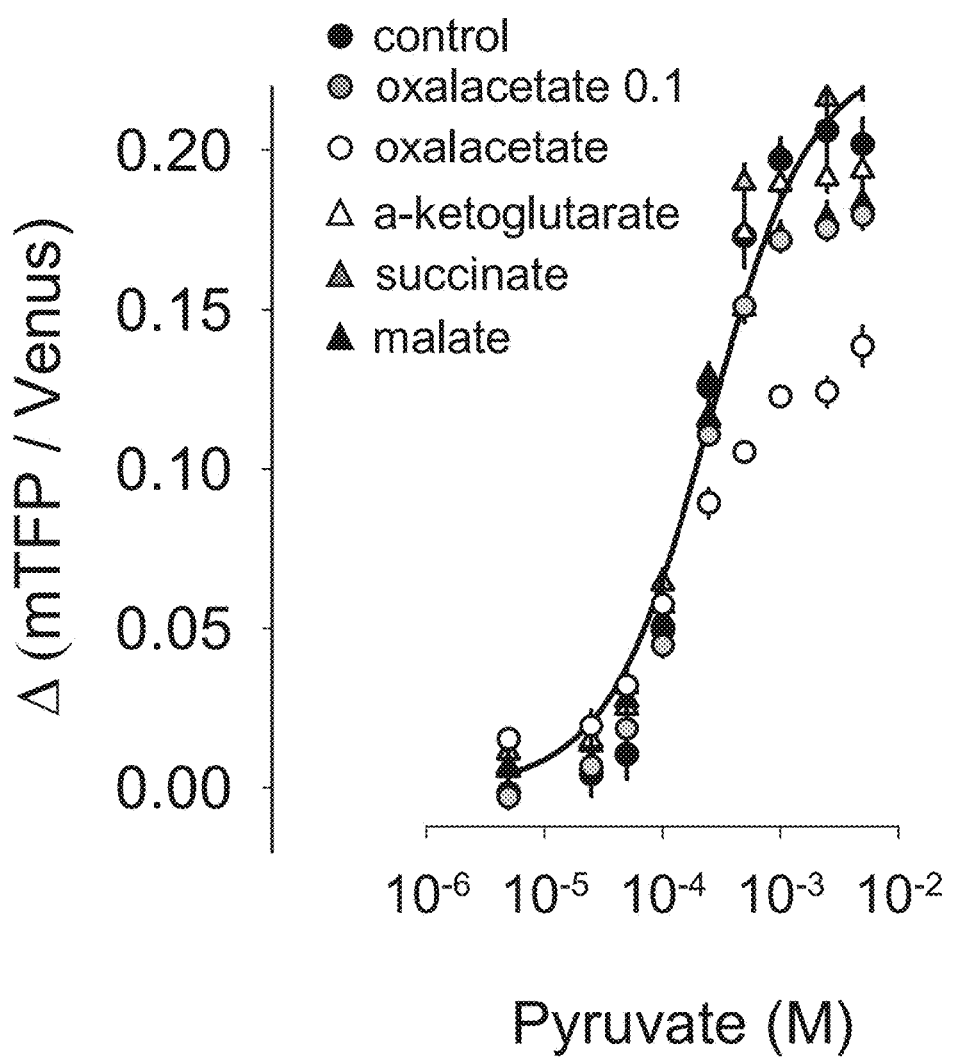
FIG. 11 shows the effect of several molecules on the response of Pyronic to pyruvate.
Figure 12:
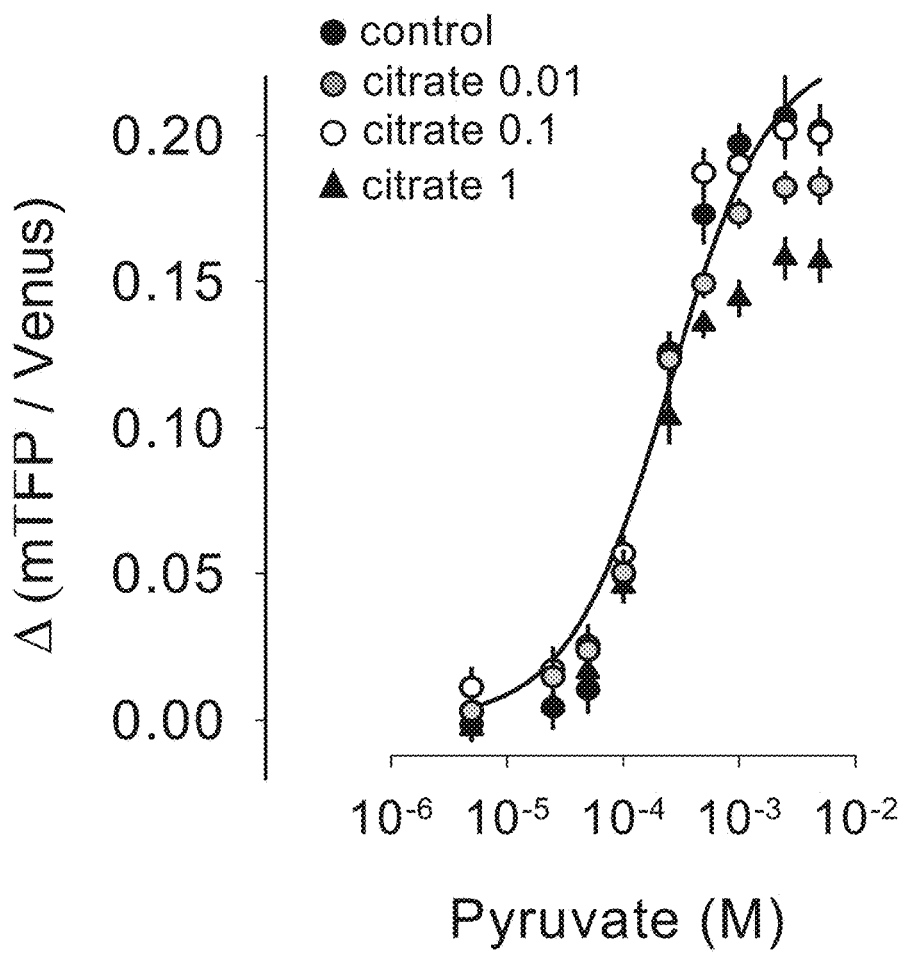
FIG. 12 shows the effect of different concentrations of citrate on the response of Pyronic to pyruvate.
Figure 13:
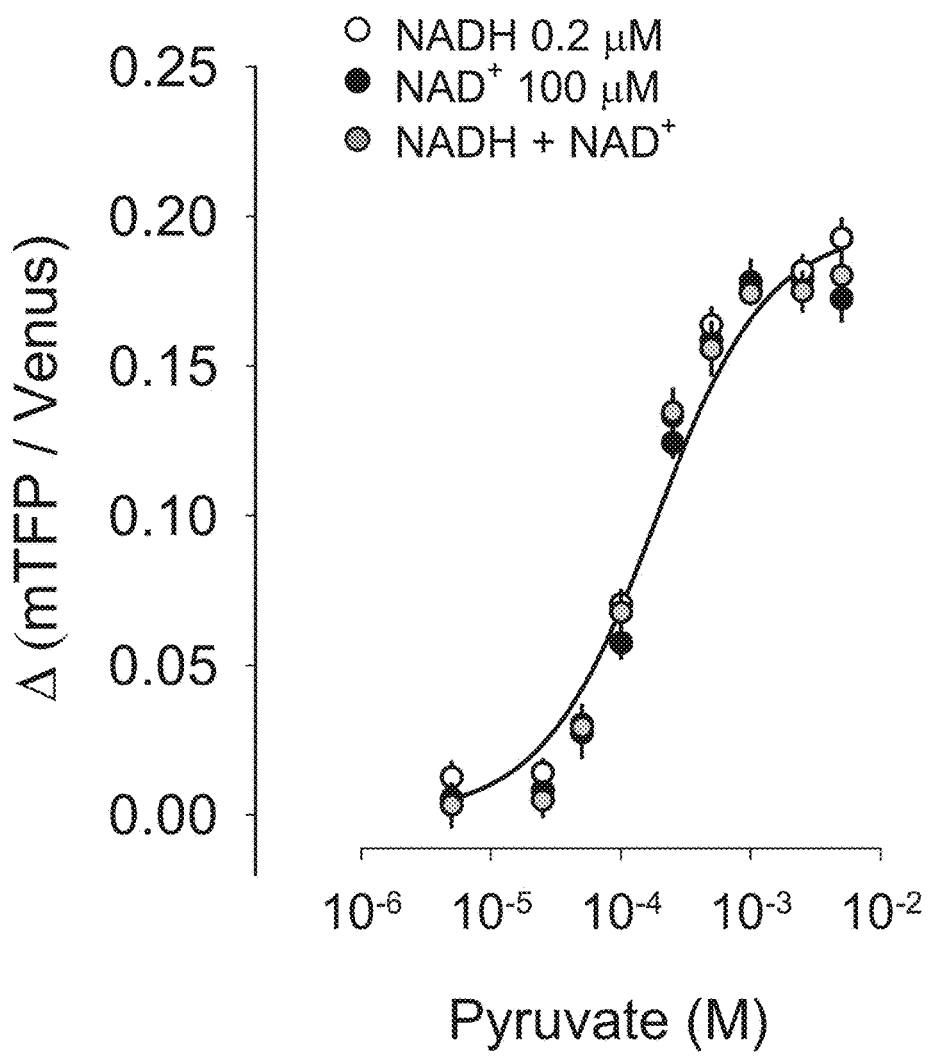
FIG. 13 shows the effect of the redox potential on the response of Pyronic to pyruvate.

The sensor showed a very small sensitivity to pH in the physiological range (FIG. 8). The specificity was investigated by exposing the sensor to high concentrations of a panel of metabolites of natural occurrence (FIG. 9). From the chosen set of molecules, citrate and oxalacetate produced a modest effect at 1 mM, and a very small at 100 μM Oxalacetate levels are in the low micromolar range and should not affect the pyruvate sensor, and cytosolic citrate levels are below 100 μM (Siess et al., 1978; Kauppinen et al., 1982), and therefore should have a negligible effect on the pyruvate sensor. Further to explore the specificity, the effect of a panel of metabolites on the response of the sensor to pyruvate was explored (FIGS. 10, 11 and 12). From the chosen set of molecules, only citrate had a significant effect of the response to pyruvate, although only at 1 mM. At 100 μM, citrate had a very small effect on the response of the sensor to pyruvate. Similar effects were observed for oxalacetate. The response of the sensor to pyruvate was insensitive to the extreme values of the redox ratio, achieved by manipulating $NAD^+$ and NADH (FIG. 13).

Figure 14:
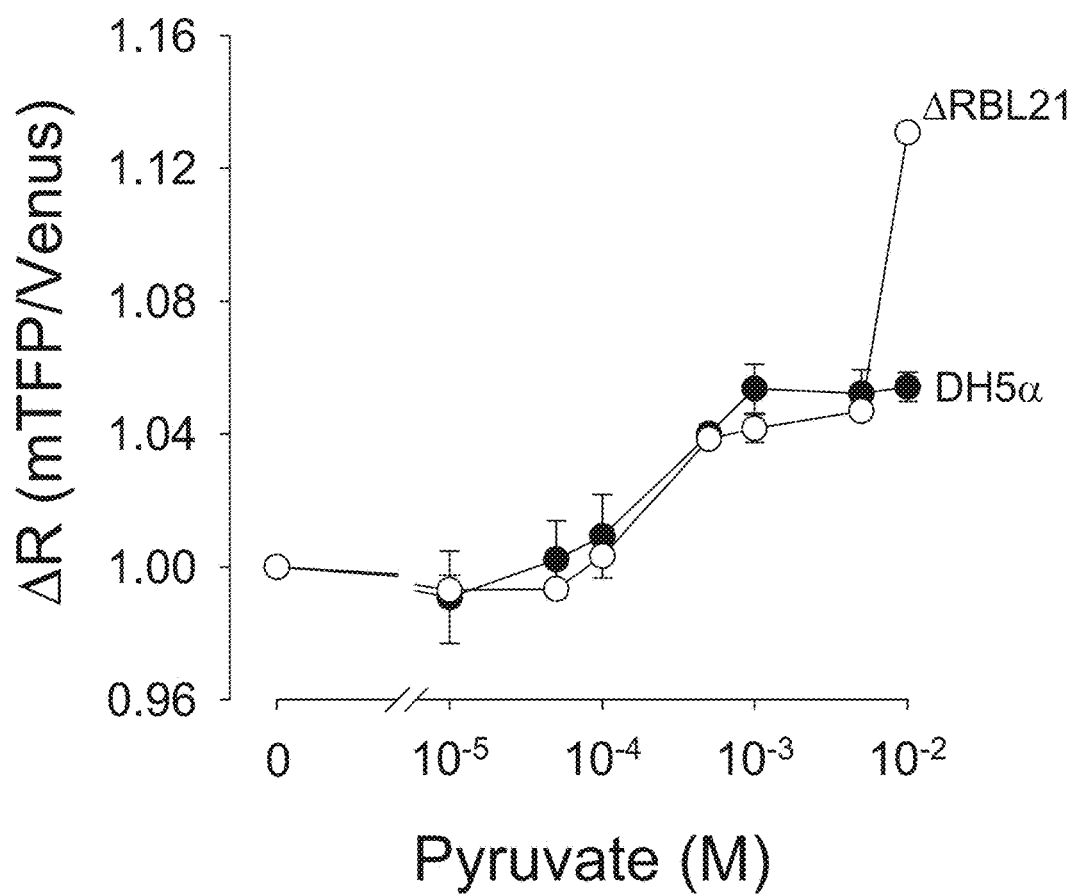
FIG. 14 shows the effect of extracellular pyruvate on the fluorescence ratio of Pyronic expressed in two different strains of *E. coli*, DH5a and BL21.
Figure 15:
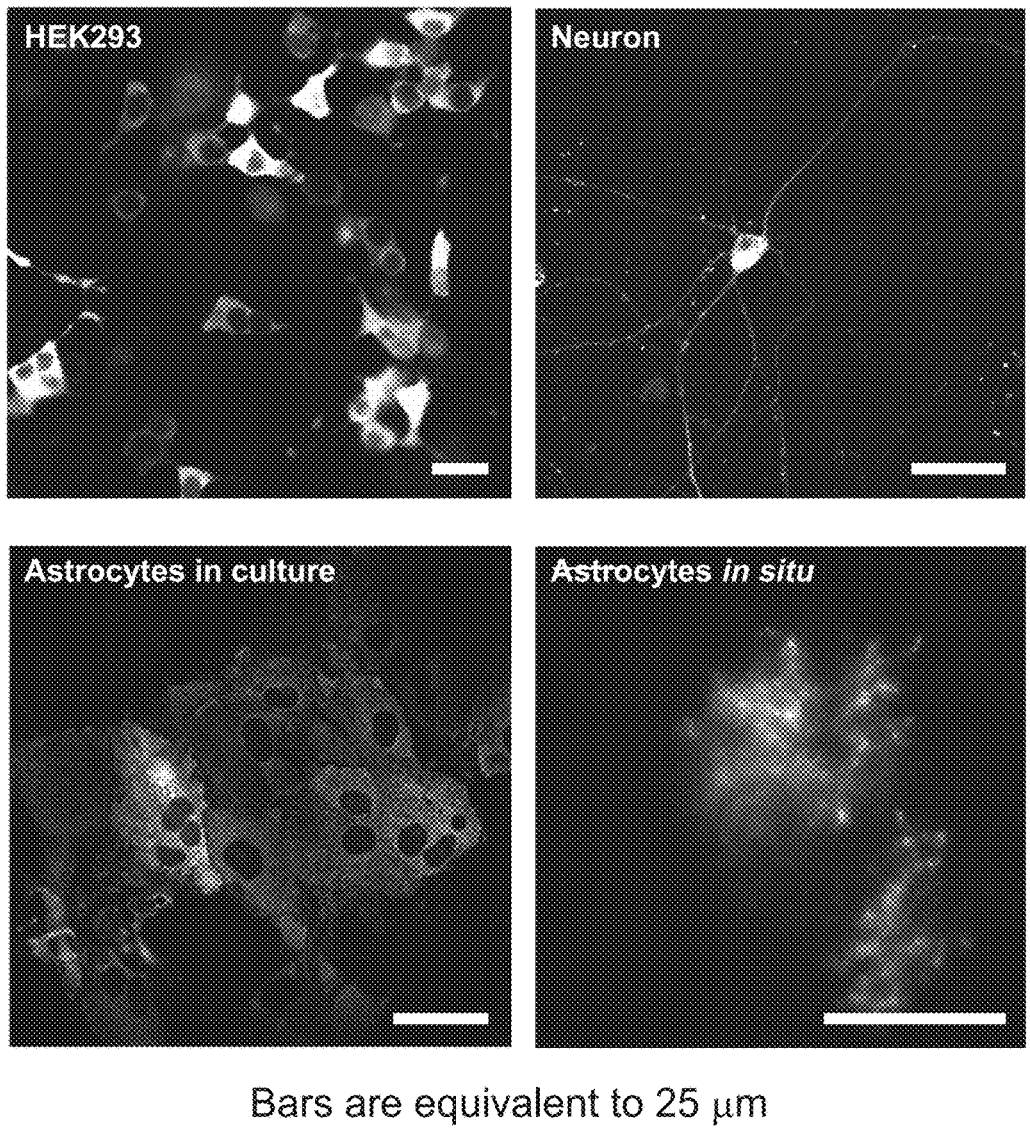
FIG. 15 shows Pyronic expressed in HEK293 cells, cultured neurons, cultured astrocytes, and astrocytes in brain tissue.
Figure 16:
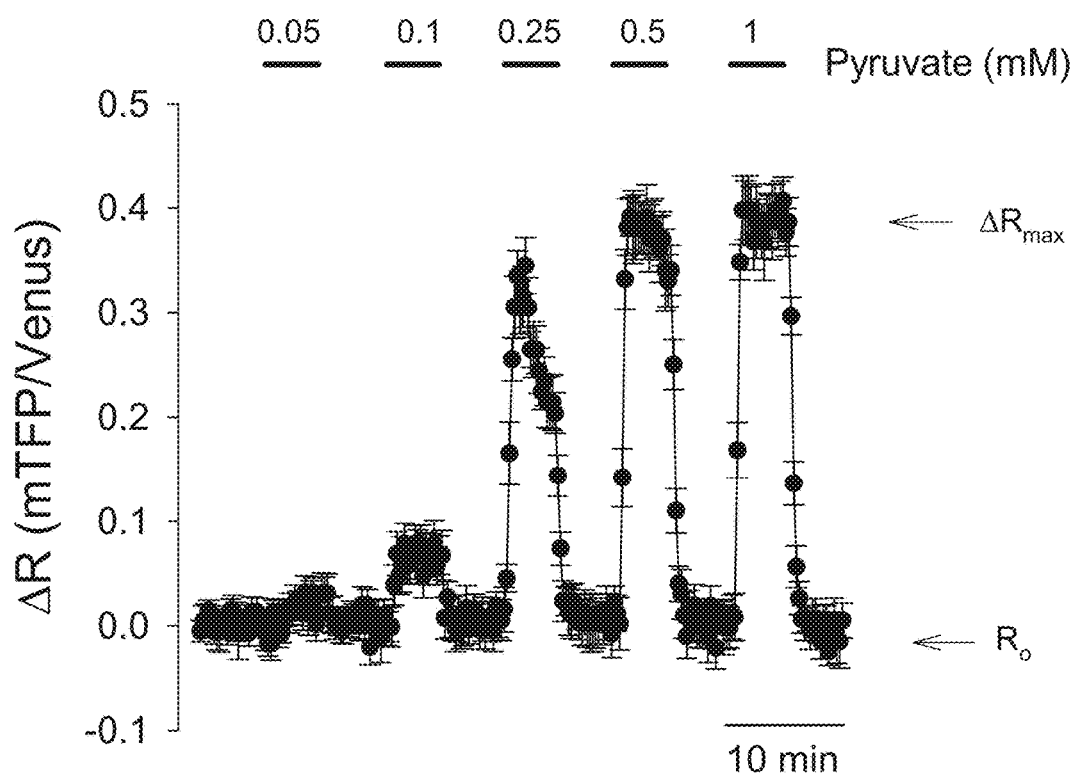
FIG. 16 shows how to obtain the values of $\Delta R_o$ and $\Delta R_{max}$ by incubating cells without pyruvate or with 1 mM pyruvate, respectively.
Figure 17:
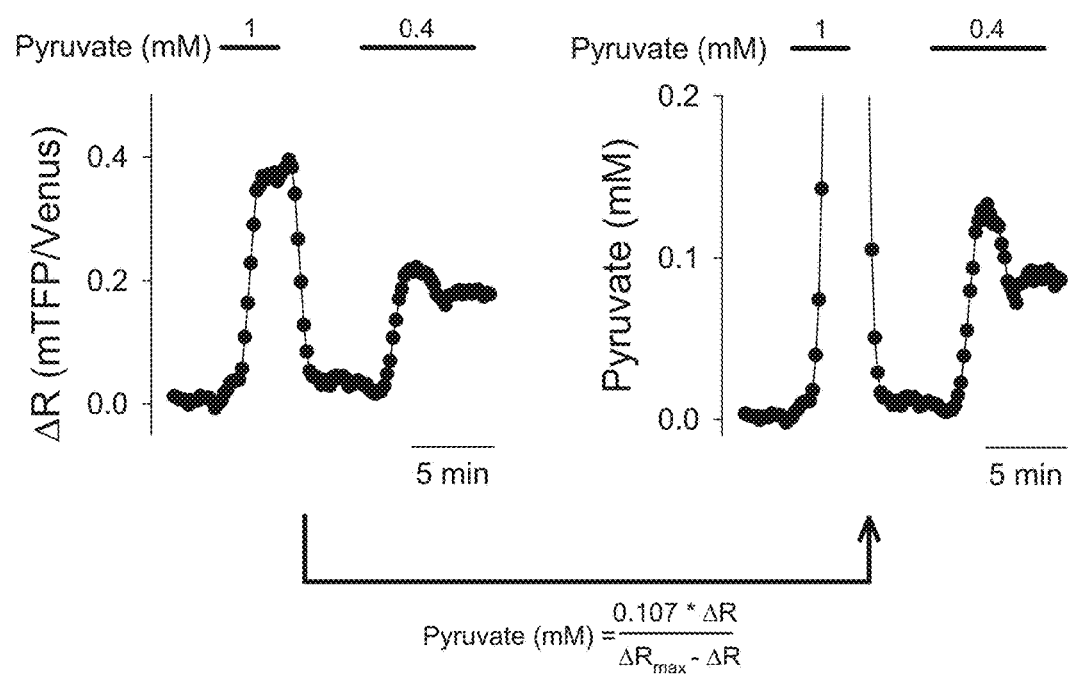
FIG. 17 illustrates a two-point calibration procedure for quantitative estimation of intracellular pyruvate with Pyronic. In the formula $R_o$ and $\Delta R_{max}$ are represented.

Expressed in *Escherichia coli*, the pyruvate sensor was sensitive to changes in extracellular pyruvate (FIG. 14), showing that intact bacteria may be used as sensors, for instance for industrial applications within bioreactors. Expressed in mammalian cells, the pyruvate sensor of the present invention distributed in the cytosol and cellular processes and was excluded from nuclei and organelles (FIG. 15). The dose-response of the sensor expressed in cells was similar to that observed in vitro, but with a larger change in FRET ratio, with typical maximum change in fluorescence ratio of 40% (FIG. 16). A two-point calibration protocol was devised that first measures the fluorescence ratio at very low pyruvate concentration, achieved by depriving the cells of glucose ($R_o$), and then measures the fluorescence ratio at saturating pyruvate by exposing the cells to 1 mM extracellular pyruvate ($R_{max}$). Having obtained the two extreme points of the saturation curve in such manner, the $K_D$ value obtained previously in vitro (107 μM) is used to transform any fluorescence ratio into pyruvate concentration by interpolation (FIG. 17).

The present invention further comprises methods using the aforementioned sensor for determination of pyruvate concentrations in samples, in single cells or cell populations, adherent cells or in suspension, in a cell culture, a tissue culture, a mixed cell culture, a tissue explant, or in animal tissues in vivo.

The method comprises the general steps of:
a) Expressing the sensor of the invention, in a desired host, such as single cells or cell populations, adherent cells or in suspension, in a cell culture, a tissue culture, a mixed cell culture, a tissue explant, or in animal tissues in vivo;
b) Calibrating the host with predetermined values of intracellular, extracellular, subcellular pyruvate concentrations, recording pyruvate concentrations in time;
c) Disrupting the steady-state of pyruvate entering the cell;
d) Recording the output from the sensor calculating the pyruvate concentration at different time points;

In the step b), corresponding to calibrating the host, the sensor of the invention is calibrated in cells using the minimum value of fluorescence ratio ($R_o$) obtained in the absence of pyruvate and glucose, the maximum value of fluorescence ratio ($\Delta R_{max}$) obtained by exposing the cells to a saturating concentration of pyruvate (>1 mM), and the affinity constant $K_D$ of the sensor obtained in vitro.

The general method can be applied in different configurations, for example, in a first embodiment; the sensor is used in a method for the measurement of the activity of the pyruvate transporter.

Figure 18:
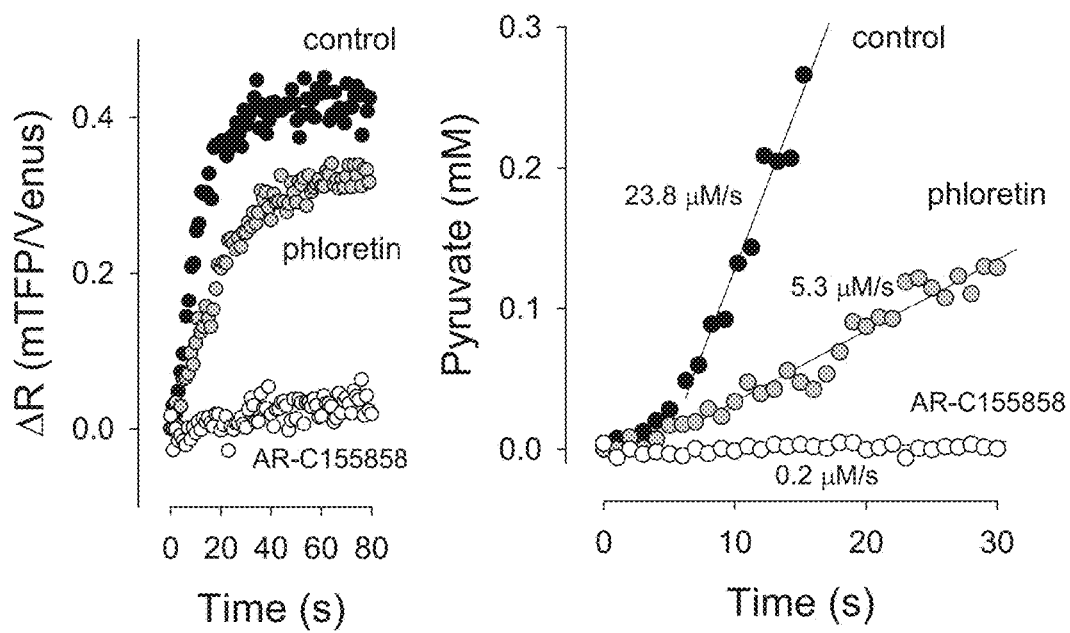
FIG. 18 shows the time course of pyruvate uptake by HEK293 cells and its inhibition by known blockers of the monocarboxylate transporter.

In this first embodiment, with the information obtained in the calibration step, the disruption of the steady-state of pyruvate entering the cell is carried out by altering the extracellular concentration of pyruvate, thus exposing the cells to pyruvate. This causes a rise in intracellular pyruvate that is monitored with the pyruvate sensor and whose initial rate is independent of pyruvate metabolism and can be used to estimate kinetic parameters (FIG. 18). Exposure of the cells to increasing concentrations of pyruvate allows the estimation of kinetic parameters for the pyruvate transporter. Kinetic parameters are also obtained from the decrease in intracellular pyruvate after removal of extracellular pyruvate. The identity of the transport pathway for pyruvate can be determined by the use of pharmacological blockers of specific transporter proteins, such as phloretin or AR-C155858 (FIG. 18 and FIG. 19), or other such as parachloromercurybenzoate, anti-MCT antisera, etc., or with compounds that interfere with the expression of specific transporter proteins, such as shRNA or siRNA, or by other similar means.

In a second embodiment, the general method can be applied to a first particular method to measure the rates of cellular pyruvate production and cellular pyruvate consumption.

In this second embodiment cells are incubated under physiological concentrations of glucose, lactate and pyruvate, and with the information obtained in the calibration step and the known sensitivity of surface pyruvate transporters to specific inhibitors, the steady-state of pyruvate is acutely disrupted by blocking the function of pyruvate transporter, for example by addition of a pharmacological blocker of the pyruvate transporter. In mammalian cells, the pyruvate transporter is the MCT and can be blocked with phloretin, parachloromercurybenzoate, AR-C155858, anti-MCT antisera, or other suitable compounds. If the cell is a net pyruvate producer, application of the MCT-blocker causes an increase in intracellular pyruvate concentration, the initial rate of which is equal to the rate of cellular pyruvate production in the steady-state. If the cell is a net pyruvate importer, application of the MCT-blocker causes a fall in intracellular pyruvate concentration, the initial rate of which is equal to the rate of pyruvate consumption on the steady-state. In cells where pyruvate transport is mediated by other transporters, the method can be applied using the appropriate inhibitors. A critical property of this sensor is that has a single component of binding so that it allows accurate quantitation of these rates. Another important property is its high temporal resolution, for only the initial rate of pyruvate accumulation is informative and after a few seconds other non-linear processes like modulation of glycolysis or mitochondrial function by pyruvate may interfere with the measurement. Because of its low temporal resolution and sensitivity, extracellular pyruvate measurement by existing techniques cannot be used in combination with MCT-blockage to estimate the rates of pyruvate production or pyruvate consumption.

In a third embodiment, the general method can be applied to a second particular method to measure the specific rate of mitochondrial pyruvate consumption.

In this third embodiment cells are incubated in pyruvate in the absence of glucose or lactate, thus forcing the mitochondria in the cells to respire using extracellular pyruvate as exclusive substrate, and with the information obtained in the calibration step, the pyruvate steady-state is acutely disrupted by blocking the function of pyruvate transporter, for example by addition of a pharmacological blocker of the pyruvate transporter. In mammalian cells, the pyruvate transporter is the MCT and can be blocked with phloretin, parachloromercurybenzoate, AR-C155858, anti-MCT antisera, or other suitable compounds. Application of the MCT-blocker causes a decrease in intracellular pyruvate concentration at a rate equal to the rate of pyruvate consumption by mitochondria. A critical property of this sensor is that has a single component of binding so that it allows accurate quantitation of these rates. Because of low temporal resolution and sensitivity, extracellular pyruvate measurement by existing techniques cannot be used in combination with MCT-blockage to estimate the rates of pyruvate production or pyruvate consumption. By measuring the rate of mitochondrial pyruvate consumption in the presence of inhibitors of different mitochondrial transporters, it is possible to ascertain the pathway whereby pyruvate enters mitochondria in specific cells.

Figure 20:
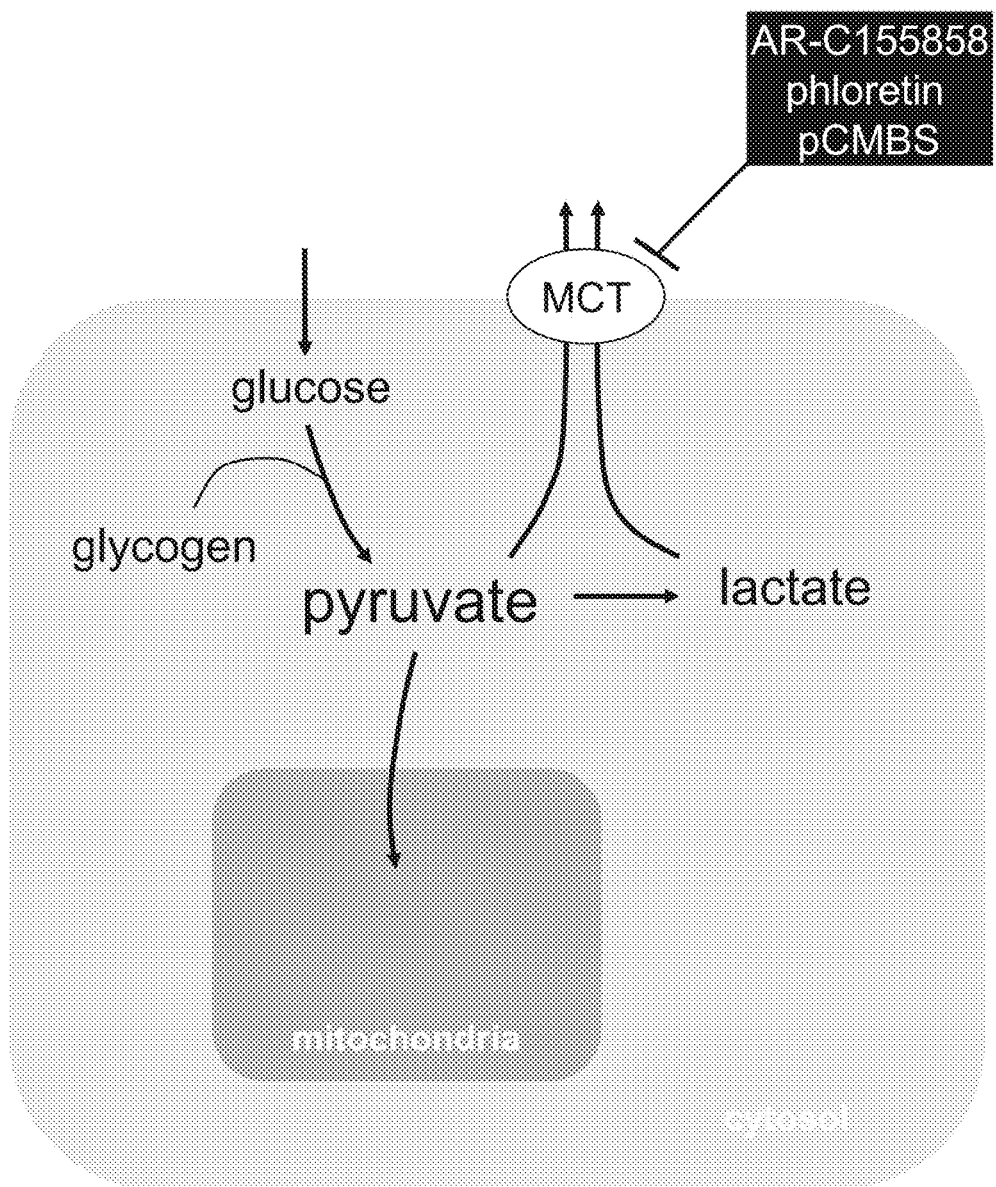
FIG. 20 depicts the main biochemical pathways for pyruvate in mammalian cells and some transporter blockers.

Based on the pyruvate sensor of this invention, methods herein disclosed, using such pyruvate sensor; allow for the first time a single-cell real-time quantification of the rates of cellular pyruvate production and cellular pyruvate consumption, as well as quantification of the rate of mitochondrial pyruvate consumption. These methods follow changes in cytosolic pyruvate concentration immediately after blockage of selected transporters. In the steady-state, the intracellular concentration of pyruvate is kept constant by a dynamic balance between glycolytic production, pyruvate efflux, pyruvate conversion into lactate and mitochondrial pyruvate consumption (FIG. 20). A perturbation of the steady-state by addition of an MCT blocker like phloretin, AR-C155858 or other, is expected to cause intracellular pyruvate accumulation at a rate equal to the rate of pyruvate production.

Figure 21:
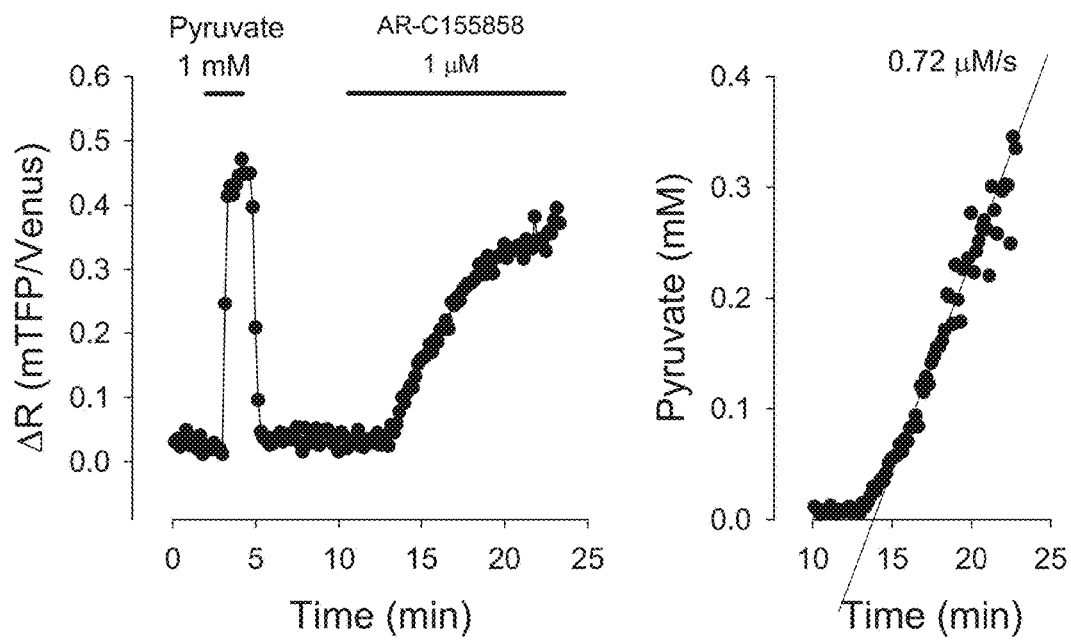
FIG. 21 demonstrates the measurement of the rate of cellular pyruvate production in HEK293 cells.
Figure 22:
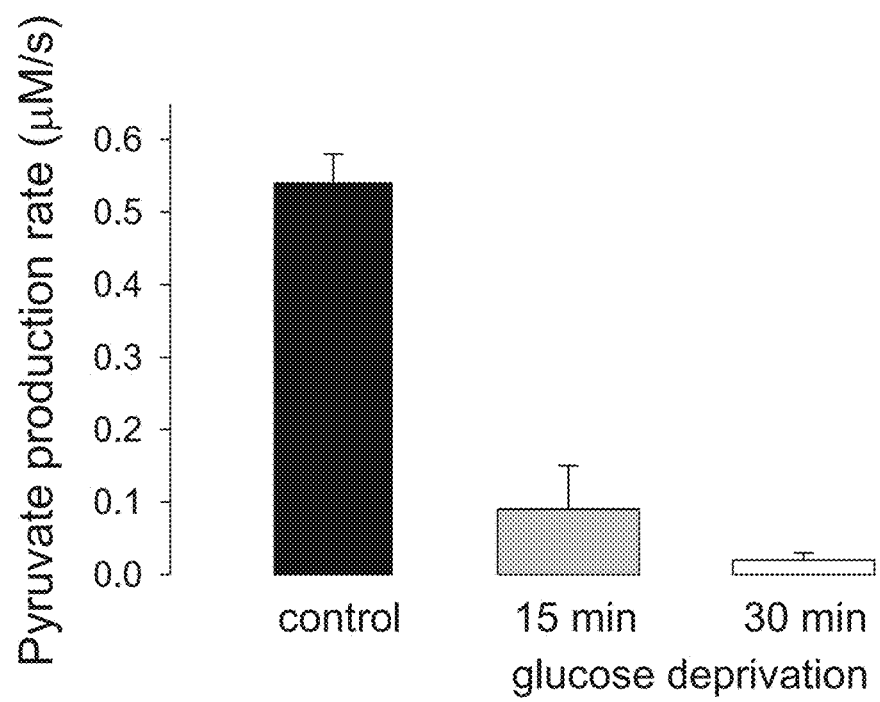
FIG. 22 shows how glucose deprivation decreases the rate of pyruvate production by HEK293 cells in time-dependent fashion.

Experimental demonstration of these methods to estimate metabolic rates is provided in FIGS. 21-24. As an example of estimation of the rate of pyruvate production, addition of the MCT blocker AR-C155858 to a single HEK293 cell caused accumulation of intracellular pyruvate at a constant rate of 0.72 $\mu$M/s (FIG. 21). On average, HEK293 cells presented a pyruvate production rate of 0.52 $\mu$M/s, which was dramatically diminished when glycolysis was inhibited by depriving the cells of glucose for increasing times (FIG. 22).

Figure 23:
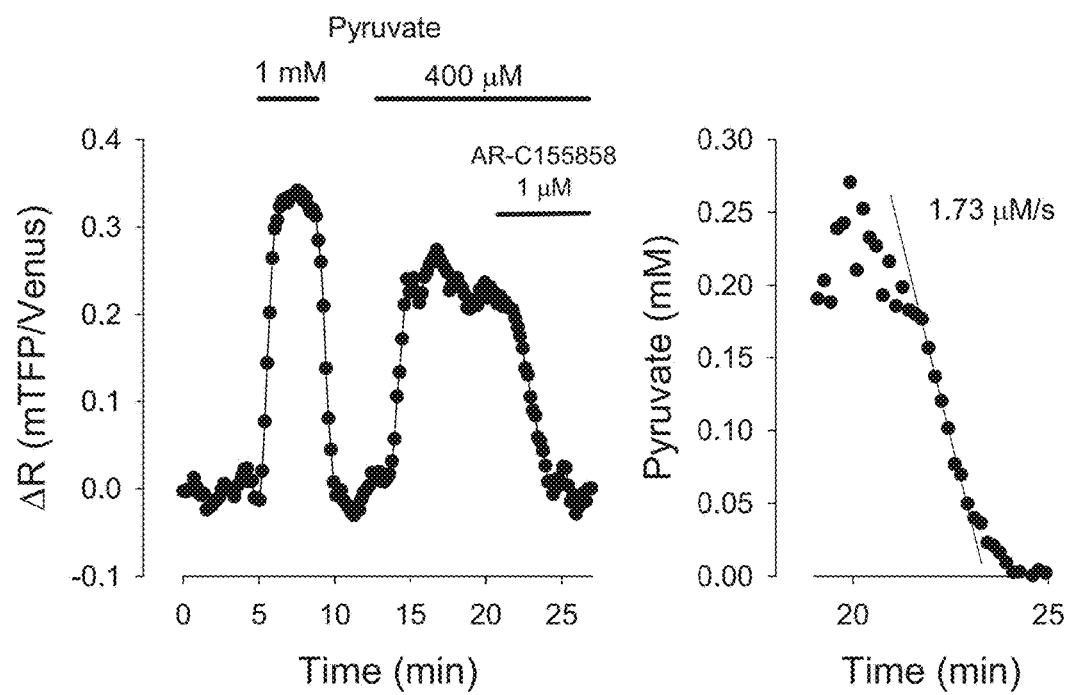
FIG. 23 demonstrates the measurement of the rate of mitochondrial pyruvate consumption using an inhibitor of the plasma membrane monocarboxylate transporter in HEK293 cells.
Figure 24:
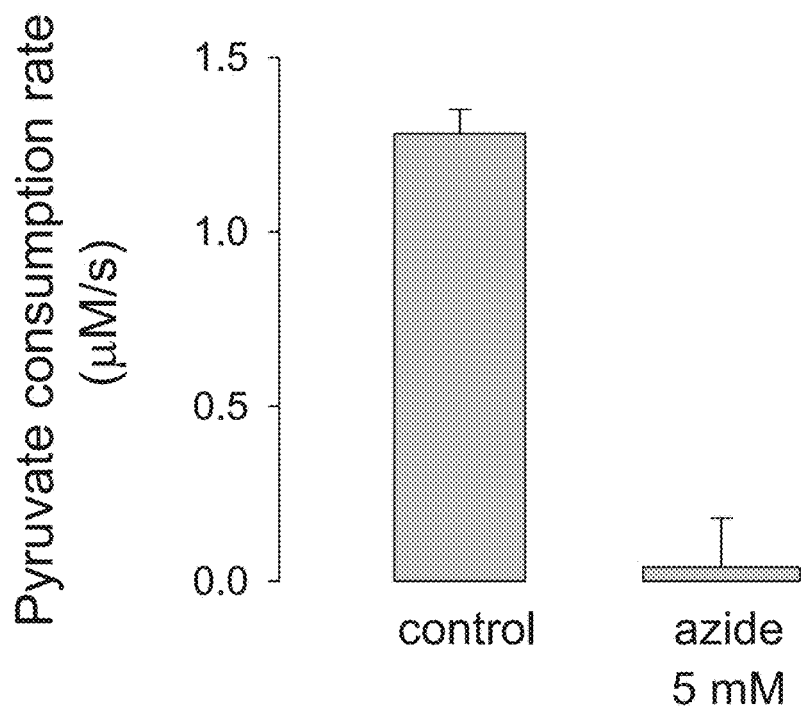
FIG. 24 shows the inhibitory effect of a blocker of mitochondrial respiration on the rate of mitochondrial pyruvate consumption in HEK293 cells.

As an example of estimation of the rate of mitochondrial pyruvate consumption, addition of the MCT blocker AR-C155858 to a single HEK293 cell in the presence of pyruvate as exclusive substrate caused a decrease in intracellular pyruvate at a constant rate of 1.73 $\mu$M/s (FIG. 23). On average, HEK293 cells presented a pyruvate consumption rate of 1.28 $\mu$M/s, which was fully inhibited in the presence of the inhibitor of mitochondrial oxidative phosphorylation sodium azide (FIG. 24).

The following examples are provided to help in the understanding of the present invention, and should not be considered a limitation to the scope of the invention.

EXAMPLES

In order to help understanding the invention, the present invention will be explained with reference to specific examples:

Protein Purification. Plasmid constructs including the SEQ ID NO 5, 6, 7 or 8, were transformed into *E. coli* BL21 (DE3). A single colony was inoculated in 100 ml of LB medium with 100 mg/ml ampicillin (without IPTG) and shaken in the dark for 2-3 days. Cells were collected by centrifugation at 5,000 rpm (4° C.) for 10 min and disrupted by sonication (Hielscher Ultrasound Technology) in 5 mL of Tris-HCl buffer pH 8.0. A cell-free extract was obtained by centrifugation at 10,000 rpm (4° C.) for 1 hour and filtering of the supernatant (0.45 $\mu$m). Proteins were purified using a Nickel resin (His Bin® from Novagen) as recommended by the manufacturer. Eluted proteins were quantified using the Biuret method and stored at −20° C. in 20% glycerol. The variant that showed the largest change in fluorescence ratio, was cloned into pcDNA3.1(−) for expression in eukaryotic cells using the restriction sites BamHI and HindIII.

Animals and Cell Cultures. Animals used were mixed F1 male mice (C57BL/6J×CBA/J), kept in an animal room under Specific Pathogen Free (SPF) conditions at a room temperature of 20±2° C., in a 12/12 h light/dark cycle with free access to food and water. Experiments were approved by the Centro de Estudios Cientificos Animal Care and Use Committee. Mixed cortical cultures of neuronal and glial cells (1-3 day-old neonates) were prepared as described (Loaiza et al., 2003). HEK293 cells were acquired from the American Tissue Culture Collection and cultured at 37° C. in 95% air/5% $CO_2$ in DMEM/F12 10% fetal bovine serum. Cultures were transfected at 60% confluence using Lipofectamine 2000 (Gibco) or alternatively, exposed to $5\times10^8$ PFU of Ad pyruvate sensor of the present invention (custom made by Vector Biolab), and studied after 24-72 h.

Fluorescence Measurements. Nickel-purified proteins were resuspended at 100 nM in an intracellular buffer containing (mM): 10 NaCl, 130 KCl, 1.25 MgSO4 and 10 HEPES, pH 7.0, and measured with a microplate reader analyzer (EnVision, PerkinElmer). The proteins were excited at 430 nm and the intensity of fluorescence emission of mTFP and Venus were recorded at 485 nm (FmTFP) and 528 nm (FVenus), respectively. The ratio (R) between FmTFP and FVenus was used to characterize the sensors. Emission spectra were obtained at 430 nm excitation, with 2 nm windows. Cells were imaged at room temperature (22-25° C.) in a 95% air/5% $CO_2$-gassed solution of the following composition (in mM): 112 NaCl, 1.25 $CaCl_2$, 1.25 MgSO4, 1-2 glucose, 10 HEPES, 24 $NaHCO^3$, pH 7.4, with 3 mM KCl (astrocytes) or 5 mM KCl (HEK and T98G) using an upright Olympus FV1000 Confocal Microscope equipped with a 20× water immersion objective (N.A. 1.0) and a 440 nm solid-state laser. Alternatively, cells were imaged with an Olympus IX70 or with an Olympus BX51 microscope equipped with a 40× oil-immersion objective (NA 1.3) or with a 20× water-immersion objective (NA 0.95). Microscopes were equipped with CAIRN monochromators (Faversham, UK), and either a Hamamatsu Orca camera controlled by Kinetics software or a Rollera camera controlled with Metafluor software, respectively. For sensor ratio measurements, cells were excited at 430 nm for 0.2-0.8 s. Emission was divided with a CAIRN Optosplit, equipped with band pass filters at 480±20 (FmTFP) and 535±15 nm (FVenus). The ratio between FmTFP and FVenus was used to measure pyruvate.

Statistical Analysis. Time courses correspond to single cells unless otherwise stated. Experiments were repeated three to six times, with 6-12 cells per experiment. Regression analyses were carried out with the computer program SigmaPlot (Jandel). Differences in mean values of paired samples were evaluated with the Student's t-test. P values <0.05 were considered significant and are indicated with an asterisk (*).

Four different variants of the pyruvate sensor, according to different embodiments of the present invention were produced. FIG. 5 shows the response to pyruvate of the four variants of the pyruvate sensor. Each of the produced variants of the pyruvate sensor of the present invention are encoded by the aminoacid sequence described in the accompanying list of sequences, wherein SEQ ID NO 1 corresponds to variant 1, SEQ ID NO 2 corresponds to variant 2, SEQ ID NO 3 corresponds to variant 3, SEQ ID NO 4 corresponds to variant 4. While SEQ ID Nos 5 to 8 correspond to the nucleic acid sequences encoding each one of the above mentioned proteins. The four variants showed a measurable change in fluorescence ratio in response to pyruvate and may be used for the different methods described in the present invention. The high rate of successful sensor generation shows a surprising robustness of PdhR as a scaffold for FRET-based sensor generation.

Figure 19:
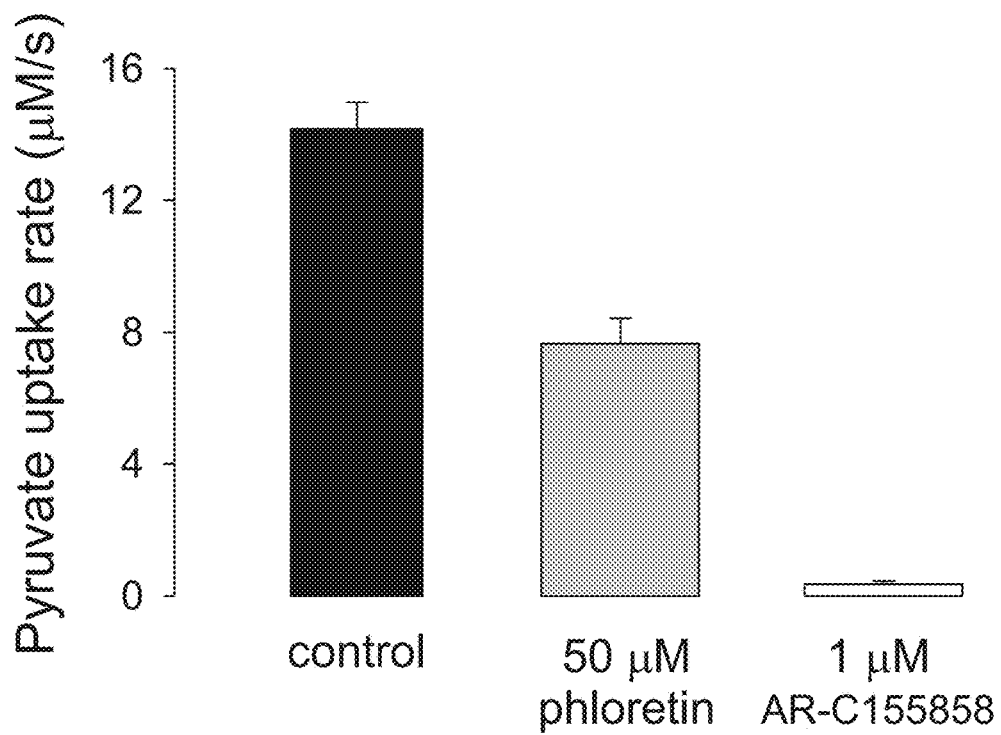
FIG. 19 summarizes pyruvate uptake rates in control HEK293 cells and in cells pretreated with known blockers of the monocarboxylate transporter.

Example 1. Method for the Measurement of Pyruvate Transporter Activity with High Spatiotemporal Resolution By controlling the exchange of pyruvate between cells and the interstitial space, MCTs are nodal points of tissue metabolism. MCTs catalyze the stoichiometric translocation of pyruvate and a proton and their activity can be measured with single-cell resolution by monitoring intracellular pH with a dye such as BCECF. However, 99.9% of protons are bound to proteins, phospholipids and other sites, and are exchanged through many transporters other than the MCT, which makes pH an imperfect proxy for pyruvate. When expressed in astrocytes, the pyruvate sensor of the present invention responded well to extracellular pyruvate, allowing real-time monitoring of pyruvate influx and efflux (FIGS. 16-17). Consistent with an MCT-mediated process, the initial rate of astrocytic uptake of 1 mM pyruvate was strongly inhibited in the presence of the specific MCT blocker AR-C155858 (1 µM) and in the presence of the broadly specific MCT blocker phloretin (50 µM) (FIGS. 18 and 19). Thus, the pyruvate sensor can be used to measure MCT activity. Pyruvate may also be transported independently of protons through gap junctions (Rouach et al., 2008) and possibly through connexin hemichannels, pannexin channels, and other channels, fluxes that are invisible to pH measurements and that may now be measured with the sensor of present invention. MCT activity may also be studied by measuring lactate fluxes with an existing lactate sensor (San Martin et al., 2013). However, lactate measurements may be ambiguous regarding pyruvate transport fluxes because the different isoforms of the MCT differ in their relative specificity for lactate and pyruvate. For example MCT1 and MCT2 are better at transporting pyruvate than lactate and MCT4 is better at transporting lactate, whereas MCT isoform expression varies between cell types and within cell types during different physiological states (Halestrap and Price, 1999).

Example 2. Measurement of the Rate of Cellular Pyruvate Production

The diagram in FIG. 20 illustrates how the intracellular concentration of pyruvate is determined by the dynamic balance between pyruvate production by glycolysis, pyruvate consumption by LDH and mitochondria, and pyruvate export through MCTs. In cells that are exporting pyruvate, perturbation of the steady state by addition of a blocker of the MCT is expected to cause pyruvate accumulation. As a demonstration of the principle, pyruvate export in HEK293 cells was blocked with AR-C155858 (1 µM), causing the expected increase in intracellular pyruvate, indicative of pyruvate production (FIG. 21). FIG. 22 shows that in the absence of extracellular glucose there is an important decrease in the rate of cellular pyruvate production; consistent with the well-established notion that pyruvate is produced from glucose.

Example 3. Method to Measure the Rate of Mitochondrial Metabolism with High Spatiotemporal Resolution in Intact Cells Pyruvate is the main mitochondrial substrate. There are no currently available methods to measure the rate of pyruvate consumption by mitochondria with high spatiotemporal resolution in intact cells or in single cells or in real time (Brand and Nicholls, 2011). In order to measure mitochondrial pyruvate consumption in intact cells, in single cells and in real time using the pyruvate sensor; cells were deprived of glucose and incubated in the presence of a high extracellular concentration of pyruvate, a condition at which the intracellular concentration of lactate becomes negligible (San Martin et al., 2013). Under such condition, a steady-state develops in which the cytosolic concentration of pyruvate remains constant due to equal influx of pyruvate into the cells and mitochondrial pyruvate consumption. Interruption of the steady-state with the blocker of the surface MCT blocker AR-C155858 results in a fall in the cytosolic pyruvate concentration at rate equal to the rate of mitochondrial pyruvate consumption (FIG. 23), which can be effectively inhibited by the reversible blocker of mitochondrial respiration sodium azide (FIG. 24).

While certain embodiments of the invention have been described, other embodiments may exist. Further, any disclosed method steps or stages may be modified in any manner, including by reordering steps and/or inserting or deleting steps, without departing from the invention. While the specification includes a detailed description of the sensor and the associated drawings, the invention's scope is indicated by the following claims. Furthermore, while the specification has been described in a specific language, the claims are not limited to the features or acts described above. Rather, the specific features and acts described above are disclosed as illustrative aspects and embodiments of the invention. Various other aspects, embodiments, modifications, and equivalents thereof which, after reading the description herein, may suggest themselves to one of ordinary skill in the art without departing from the spirit of the present invention or the scope of the claimed subject matter.

What is claimed is:

1. A Forster Resonance Energy Transfer (FRET)-based pyruvate sensor comprising a bacterial PdhR transcription factor between any suitable donor and acceptor fluorescent proteins moieties that are capable in combination of serving as donor and acceptor moieties in FRET, which can be expressed in single cells or cell populations, adherent cells or in suspension, in a cell culture, a tissue culture, a mixed cell culture, a tissue explant, or in animal tissues in vivo, wherein the FRET-based pyruvate sensor has at least 60%, 70%, 80% 85%, 90%, 95%, or 99% amino acid sequence identity with SEQ ID NO: 1, SEQ ID NO: 2, SEQ ID NO: 3, or SEQ ID NO: 4.

2. FRET-based pyruvate sensor according to claim 1, wherein the fluorescent proteins moieties are selected from the group consisting of mTFP (monomeric teal fluorescent protein), CFP (cyan fluorescent protein), BFP (blue fluorescent protein), GFP (green fluorescent protein), YFP (yellow fluorescent protein), enhanced variations thereof such as enhanced YFP (EYFP), Citrine, Venus, or infrared fluorescent proteins from bacterial and plant phytochromes.

3. FRET-based pyruvate sensor according to claim 1, wherein the fluorescent proteins moieties are mTFP and Venus.

4. A Forster Resonance Energy Transfer (FRET)-based pyruvate sensor comprising a bacterial PdhR transcription factor between any suitable donor and acceptor fluorescent proteins moieties that are capable in combination of serving as donor and acceptor moieties in FRET, which can be expressed in single cells or cell populations, adherent cells or in suspension, in a cell culture, a tissue culture, a mixed cell culture, a tissue explant, or in animal tissues in vivo, wherein the FRET-based pyruvate sensor is encoded by the nucleic acid sequences having at least 60%, 70%, 80% 85%, 90%, 95%, or 99% sequence identity with SEQ ID NO: 5, SEQ ID NO: 6, SEQ ID NO: 7, or SEQ ID NO: 8.

5. A method for the measurement of pyruvate wherein the method comprises the steps of:
   a. Expressing a FRET-based pyruvate sensor of claim 1 in a desired host, such as single cells or cell populations, adherent cells or in suspension, in a cell culture, a tissue culture, a mixed cell culture, a tissue explant, or in animal tissues in vivo;
   b. Calibrating the host with predetermined values of intracellular, extracellular, subcellular pyruvate concentrations, recording pyruvate concentrations in time;
   c. Disrupting the steady-state of pyruvate in the cell;
   d. Recording the output from the sensor calculating the pyruvate concentration at different time points and determining the rates of transport.

6. Method for the measurement of pyruvate according to claim 5, wherein in step b) the FRET-based pyruvate sensor of the invention is calibrated in cells using the minimum value of fluorescence ratio obtained in the absence of pyruvate and glucose, the maximum value of fluorescence ratio obtained by exposing the cells to a saturating concentration of pyruvate, and the affinity constant KD of the sensor obtained in vitro.

7. Method for the measurement of pyruvate according to claim 6, wherein in step c) the disruption of the steady-state of pyruvate entering the cell is carried out by altering the extracellular concentration of pyruvate, thus exposing the cells to pyruvate.

8. A method for the measurement of the rates of pyruvate production or consumption wherein the method comprises the steps of:
   a. Expressing a FRET-based pyruvate sensor of claim 1 in a desired host, such as single cells or cell populations, adherent cells or in suspension, in a cell culture, a tissue culture, a mixed cell culture, a tissue explant, or in animal tissues in vivo;
   b. Calibrating the host with predetermined values of intracellular, extracellular, subcellular pyruvate concentrations, recording pyruvate concentrations in time;
   c. Disrupting the steady-state of pyruvate in the cell;
   d. Recording the output from the sensor calculating the pyruvate concentration at different time points and determining the rates of transport.

9. Method for the measurement of the rate of pyruvate production or consumption according to claim 8, wherein in step b) the FRET-based pyruvate sensor is calibrated in cells using the minimum value of fluorescence ratio obtained in the absence of pyruvate and glucose, the maximum value of fluorescence ratio obtained by exposing the cells to a saturating concentration of pyruvate, and the affinity constant KD of the sensor obtained in vitro.

10. Method for the measurement of the rate of pyruvate production or consumption according to claim 8, wherein in step c) the pyruvate steady-state is disrupted by addition of a blocker of the pyruvate transporter which causes an increase in intracellular pyruvate concentration rate, the initial rate of which is equal to the rate of cellular pyruvate production in the steady-state; or causes a fall in intracellular pyruvate concentration, the initial rate of which is equal to the rate of pyruvate consumption in the steady-state.

11. A method for the measurement of the rate of mitochondrial pyruvate consumption wherein the method comprises the steps of:
   a. Expressing a FRET-based pyruvate sensor of claim 1 in a desired host, such as single cells or cell populations, adherent cells or in suspension, in a cell culture, a tissue culture, a mixed cell culture, a tissue explant, or in animal tissues in vivo;
   b. Calibrating the host with predetermined values of intracellular, extracellular, subcellular pyruvate concentrations, recording pyruvate concentrations in time;
   c. Disrupting the steady-state of pyruvate in the cell;
   d. Recording the output from the sensor calculating the pyruvate concentration at different time points and determining the rates of transport.

12. Method for the measurement of the rate of mitochondrial pyruvate consumption according to claim 11, wherein in step b) the FRET-based pyruvate sensor is calibrated in cells using the minimum value of fluorescence ratio obtained in the absence of pyruvate and glucose, the maximum value of fluorescence ratio obtained by exposing the cells to a saturating concentration of pyruvate, and the affinity constant KD of the sensor obtained in vitro.

13. Method for the measurement of the rate of mitochondrial pyruvate consumption according to claim 11, wherein in step c) the disruption of pyruvate steady-state is by adding a blocker of the mitochondrial pyruvate transporter and causes a decrease in intracellular pyruvate concentration equal to the rate of pyruvate consumption by mitochondria.

14. FRET-based pyruvate sensor according to claim 4, wherein the fluorescent proteins moieties are selected from the group consisting of mTFP (monomeric teal fluorescent protein), CFP (cyan fluorescent protein), BFP (blue fluorescent protein), GFP (green fluorescent protein), YFP (yellow fluorescent protein), enhanced variations thereof such as enhanced YFP (EYFP), Citrine, Venus, or infrared fluorescent proteins from bacterial and plant phytochromes.

15. FRET-based pyruvate sensor according to claim 4, wherein the fluorescent proteins moieties are mTFP and Venus.

* * * * *